US012064640B2

(12) United States Patent
Clark et al.

(10) Patent No.: US 12,064,640 B2
(45) Date of Patent: Aug. 20, 2024

(54) RESPONSE MECHANISMS

(71) Applicant: ZOLL Medical Corporation, Chelmsford, MA (US)

(72) Inventors: John Clark, Pittsburgh, PA (US); Mark Roberto, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 18/130,017

(22) Filed: Apr. 3, 2023

(65) Prior Publication Data
US 2023/0347158 A1 Nov. 2, 2023

Related U.S. Application Data

(63) Continuation of application No. 16/230,097, filed on Dec. 21, 2018, now Pat. No. 11,642,539.

(51) Int. Cl.
*A61N 1/39* (2006.01)
*A61B 5/00* (2006.01)
*A61B 5/318* (2021.01)
*A61N 1/36* (2006.01)
*A61N 1/365* (2006.01)
*G16H 20/30* (2018.01)

(52) U.S. Cl.
CPC .............. *A61N 1/395* (2013.01); *A61B 5/318* (2021.01); *A61B 5/4836* (2013.01); *A61B 5/746* (2013.01); *A61N 1/36135* (2013.01); *A61N 1/36514* (2013.01); *A61N 1/3904* (2017.08); *A61N 1/3987* (2013.01); *A61N 1/3925* (2013.01); *G16H 20/30* (2018.01)

(58) Field of Classification Search
CPC ................ A61N 1/395; A61N 1/36135; A61N 1/36514; A61N 1/3904; A61N 1/3987; A61N 1/3925; A61N 1/3993; A61B 5/318; A61B 5/4836; A61B 5/746; A61B 5/361
See application file for complete search history.

(56) References Cited

U.S. PATENT DOCUMENTS 6,636,732 B1 10/2003 Boling et al.
8,717,141 B2 5/2014 Eberhart et al.
(Continued)

OTHER PUBLICATIONS

"LifeVest System WCD 3100 Patient Manual," 2015, ZOLL Medical Corporation <https://www.accessdata.fda.gov/cdrh_docs/pdf/P010030S056c.pdf> (Previously submitted in related U.S. Appl. No. 16/230,097).

(Continued)

Primary Examiner — Mallika D Fairchild
(74) Attorney, Agent, or Firm — Gardella Grace P.A.

(57) ABSTRACT

A wearable medical device is provided for monitoring the cardiac health of a patient, for example, for indications of cardiac anomalies, where the device includes ECG sensors in electrical contact with the patient's body, therapy electrodes for providing electrical therapy to the patient's heart, and a control unit having at least one touch control with force sensor disposed on its housing for contacting with a finger. Signals from the touch control may be analyzed to identify force application below a first force threshold and at or above a second force threshold below the first force threshold, and, responsive to detecting such application of force, user input may be registered. User inputs to the at least one touch control may be used to delay therapy by the therapy electrodes.

20 Claims, 12 Drawing Sheets

(56) References Cited

U.S. PATENT DOCUMENTS

| | | | |
|---|---|---|---|
| 8,797,295 | B2 | 8/2014 | Bernstein et al. |
| 11,642,539 | B2 | 5/2023 | Clark et al. |
| 2006/0132283 | A1 | 6/2006 | Eberhart et al. |
| 2008/0306562 | A1 | 12/2008 | Donnelly et al. |
| 2009/0227223 | A1 | 9/2009 | Jenkins |
| 2010/0328230 | A1 | 12/2010 | Faubert et al. |
| 2011/0227872 | A1 | 9/2011 | Huska et al. |
| 2011/0248948 | A1 | 10/2011 | Griffin et al. |
| 2015/0039053 | A1 | 2/2015 | Kaib et al. |
| 2017/0021184 | A1 | 1/2017 | Pavel et al. |
| 2017/0056682 | A1 | 3/2017 | Kumar et al. |
| 2017/0188979 | A1 | 7/2017 | Volpe |
| 2020/0197713 | A1 | 6/2020 | Clark et al. |

OTHER PUBLICATIONS

Non-Final Office Action mailed in U.S. Appl. No. 16/230,097 dated Oct. 27, 2021.
Final Office Action mailed in U.S. Appl. No. 16/230,097 dated Apr. 5, 2022.
Non-Final Office Action mailed in U.S. Appl. No. 16/230,097 dated Jul. 29, 2022.
Notice of Allowance mailed in U.S. Appl. No. 16/230,097 dated Jan. 4, 2023.
Corrected Notice of Allowability mailed in U.S. Appl. No. 16/230,097 dated Jan. 9, 2023.

RESPONSE MECHANISMS

RELATED APPLICATIONS

This application is a continuation of and claims priority to U.S. patent application Ser. No. 16/230,097, entitled "Response Mechanisms," filed Dec. 21, 2018, which is incorporated by reference herein in its entirety.

BACKGROUND

The present disclosure is directed to wearable medical devices for ongoing monitoring of a patient and, in particular, a patient's heart functioning. There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Wearable medical monitoring and/or treatment devices such as wearable cardioverter defibrillator (WCD) devices operate by applying corrective electrical pulses directly to the patient's heart. Ventricular fibrillation or ventricular tachycardia can be treated, for example, by providing a therapeutic shock to the heart in an attempt to restore normal rhythm. To treat conditions such as bradycardia, tachycardia, or asystole the wearable medical device can provide pacing stimuli to the patient's heart until intrinsic cardiac electrical activity returns.

A patient wearing the wearable medical device may interact with the device. For example, the device can request that the patient provide a response to confirm one or more actions to be taken by the device. In one example, the wearable device may prompt the patient to provide a response prior to any delivery of a therapeutic shock. If the patient provides a response, the device may suspend or cancel the therapeutic shock. If the patient does not provide a response, the device may escalate its prompts and/or proceed to deliver the therapeutic shock. In other scenarios, the wearable device may prompt the patient to provide input relating to information recorded by the device. For example, the patient can respond to audible or visual prompts and/or surveys provided by the wearable medical device.

SUMMARY

Techniques, methods, systems, and devices are described herein relating to response mechanisms for interacting with a wearable medical device.

In one aspect, the present disclosure relates to a wearable medical device including a number of ECG sensors configured to be in electrical contact with a body of a patient, a number of therapy electrodes configured to provide electrical therapy to a heart of the patient, and a control unit connected to the number of ECG sensors and the number of therapy electrodes, the control unit including a housing. At least one touch control may be disposed on the housing, where the at least one touch control is configured to be contacted with a finger of the patient, and the at least one touch control includes a force sensor. The wearable medical device may include a memory and a processor in communication with the memory. The processor may be configured to monitor, over a predetermined period of time, for a user input based on signals from the at least one touch control, where the monitoring includes analyzing a first signal from the at least one touch control to identify application of a user force at the force sensor, responsive to determining that a force value of the user force is below a first predetermined force threshold, determining whether the force value is at or above a second predetermined force threshold that is below the first predetermined force threshold, and responsive to detecting application of the user force at or above the second predetermined force threshold and below the first predetermined force threshold, register the user input.

In some implementations, the processor is configured to, after registering the user input, verify the user input. The processor may be configured to verify the user input by requesting that the patient provide, during a second predetermined period of time, a second user input. The second user input may include a voice input provided by the patient. The second user input may include at least one of application of a second user force at the force sensor at or above the first predetermined force threshold during the second predetermined period of time, and application of the second user force at the force sensor at or above the second predetermined force threshold and below the first predetermined force threshold during the second predetermined period of time. The second user input may include at least one of a) a pulsed force persisting throughout the second predetermined period of time, each pulse of the pulsed force at or exceeding the second predetermined force threshold, and b) a predetermined pattern of applied forces, each force of the predetermined pattern of applied forces at or exceeding the second predetermined force threshold.

In some implementations, the processor is configured to, prior to monitoring for the user input, provide the patient with a notification regarding commencement of a treatment. Monitoring for the user input may include, after registering the user input, verifying the user input is to activate a failsafe override of the treatment, and upon the determining, delaying the treatment. Verifying the user input is to activate the failsafe override of the treatment may include analyzing, over a second predetermined period of time, a number of signals from the at least one touch control, identifying, from the number of signals, at least one of a) a pulsed force persisting throughout the second predetermined period of time, each pulse of the pulsed force at or exceeding the second predetermined force threshold, and b) a predetermined pattern of applied forces, each force of the predetermined pattern of applied forces at or exceeding the second predetermined force threshold, and, upon the identifying, delaying the treatment. Identifying the predetermined pattern of applied forces may include outputting a message to the patient for applying the predetermined pattern. Outputting the message may include activating a number of time-spaced haptic outputs to the at least one touch control or the surface of the medical device for coordinating patient-applied forces responsive to each haptic output of the number of time-spaced haptic outputs. The predetermined pattern of applied forces may include at least one slow application of force to the at least one touch control, the at least one slow application of force including a first slow application of force including a number of forces of increasing intensity, each force of the number of forces being within a range from the second predetermined force threshold to the first predetermined force threshold. The at least one slow application of force may further include a second slow application of force including a number of forces of decreasing intensity, where the second slow application of force directly follows the first slow application of force. The pulsed force may include at least five discrete applications of force each within a range from the second predetermined force threshold to the first predetermined force threshold.

In some implementations, the first predetermined force threshold is in a range from 400 g-f to 1000 g-f. The second predetermined force threshold may be in a range from 80 g-f to 400 g-f. A differential between the first predetermined force threshold and the second predetermined force threshold may be between 0 and 20 g-f.

In one aspect, the present disclosure relates to a wearable medical device for providing treatment to a patient responsive to monitoring the patient, the wearable medical device including a number of ECG sensors configured to be in electrical communication with a body of the patient, a number of therapy electrodes configured to provide electrical therapy to a heart of the patient, and a control unit in communication with the number of ECG sensors and the number of therapy electrodes. The control unit may include a housing, two or more touch controls each configured to be contacted with a finger of the patient, the two or more touch controls including a first touch control including a force sensor, and a second touch control including a force-activated switch. The wearable medical device may include monitoring circuitry in communication with a number of ECG sensors and the two or more touch controls, a non-transitory computer-readable memory in communication with the monitoring circuitry, and at least one processor in communication with the non-transitory computer-readable memory and the monitoring circuitry. The at least one processor may be configured to detect, via the number of ECG sensors, an indication of a cardiac anomaly in the patient, provide the patient with a notification regarding commencement of the treatment in response to detecting the indication of the cardiac anomaly, and, after providing the notification to the patient, monitor, over a predetermined period of time, signals from the first touch control and the second touch control. The monitoring may include analyzing a first signal from the force sensor of the first touch control to identify a force value below a first threshold level of force and at or above a second threshold level of force, and analyzing a second signal from the second touch control to identify actuation of the force-activated switch. The at least one processor may be configured to, responsive to detecting actuation of the force-activated switch of the second touch control and application of the force value at the first touch control, delaying the treatment.

In some implementations, the first touch control is disposed on a first surface of the housing, and the second touch control is disposed on a second surface of the housing. The first surface may be opposite the second surface of the housing such that the first touch control and the second touch control are configured to be simultaneously activated with a pinching motion of a hand of the patient. The first touch control and the second touch control may each be disposed proximate or within a respective depression within the respective surface of the housing to guide the finger of the patient toward the respective touch control.

In some implementations, the first threshold level of force is in a range from 400 g-f to 1000 g-f. The second threshold level of force may be in a range from 80 g-f to 400 g-f. A differential between the first threshold level of force and the second threshold level of force may be at least 100 g-f.

In some implementations, delaying the treatment includes delaying the treatment responsive to detecting actuation of the force-activated switch of the second touch control along with application of the force value at the first touch control. Analyzing the first signal may include analyzing a first time-series of signals from the force sensor of the first touch control to identify the force value as a force applied over a threshold period of time.

In some implementations, the second touch control includes a second force sensor, and monitoring the signals from the first touch control and the second touch control includes analyzing a third signal from the second force sensor. The monitoring may include, responsive to detecting application of a second force value below the first threshold level of force and at or above the second threshold level of force to the second touch control along with application of the force value to the first touch control, delaying the treatment. The first touch control may include a second force-activated switch, and the at least one processor may be configured to, over the predetermined period of time, upon detecting application of a second force value below the first threshold level of force and at or above the second threshold level of force to the second touch control along with actuation of the force-activated switch of the first touch control, delay the treatment. The second threshold level of force may be less than or equal to a force required for actuation of the second force-activated switch.

In some implementations, the at least one processor is configured to delay the treatment responsive to detecting actuation of the second touch control along with continuous application of force below the first threshold level of force and at or above the second threshold level of force to the first touch control for a threshold period of time.

In some implementations, the at least one processor is configured to delay the treatment responsive to detecting actuation of the second touch control along with intermittent application of force below the first threshold level of force and at or above the second threshold level of force to the first touch control over a threshold window of time. The intermittent application of force may occur at least every 60 seconds. The threshold window of time may be between 15 to 60 seconds.

In some implementations, the at least one processor is configured to, prior to detecting the indication of the cardiac anomaly, conduct a calibration sequence including detecting actuation of one of the first touch control and the second touch control along with application of at least the threshold force to the other of the first touch control and the second touch control, after the detecting, monitoring signals from the first touch control and the second touch control over a calibration period of time to determine an activation profile of the patient; and storing at least one of the activation profile and an identification of an activation threshold force in the non-transitory computer readable memory. Detecting the application of below the first threshold level of force and at or above the second threshold level of force to the first touch control may include detecting the application of at least the below the first threshold level of force and at or above the second threshold level of force based in part on the at least one of the activation profile and the identification of the activation threshold force. Conducting the calibration sequence may include repeating the detecting, the monitoring, and the storing, and determining the at least one of the activation profile and the identification of an activation threshold force based upon data obtained through the repeating.

In some implementations, at least one of the first threshold level of force and the second threshold level of force is determined based on calibration data obtained through a calibration exercise with the patient. The at least one processor may be configured to periodically initiate the calibration exercise. The at least one processor may be configured to conduct a calibration sequence outside the calibration exercise and during routine user interaction with the control unit in order to determine typical force applied to the first touch control, and adjust at least one of the first threshold level of force and the second threshold level of force based on the calibration sequence.

In some implementations, the at least one processor is configured to adjust at least one of the first threshold level of force and the second threshold level of force based on signals received from at least one of an accelerometer, a gyroscope, and a magnetometer in communication with the control unit.

In some implementations, the wearable medical device is releasably affixed to a torso of the patient using an adhesive.

In one aspect, the present disclosure relates to a method for monitoring and providing treatment to a patient wearing a medical device, the method including receiving, by monitoring circuitry in communication with a number of ECG sensors in electrical communication with a body of the patient, a number of monitoring signals, where a control unit includes the monitoring circuitry, detecting, by at least one processor of the control unit, an indication of cardiac anomaly in the patient evidenced by the number of monitoring signals, and providing, via an output device of the control unit, a notification for the patient regarding commencement of the treatment. The method may include, after providing the notification to the patient, monitoring, over a predetermined period of time with the monitoring circuitry, signals from two or more touch controls, where each touch control of the two or more touch controls is configured to be contacted with a finger of the patient, the two or more touch controls including a first touch control including a force sensor, and a second touch control including an force-activated switch. Monitoring may include analyzing a first signal from the force sensor of the first touch control to identify a force value below a first threshold level of force and at or above a second threshold level of force, and analyzing a second signal from the second touch control to identify actuation of the force-activated switch. The method may include, responsive to detecting actuation of the force-activated switch of the second touch control and application of the force value at the first touch control, delaying the treatment.

In some implementations, the first touch control is disposed on a first surface of a housing of the control unit, and the second touch control is disposed on a second surface of the housing. The first surface may be opposite the second surface of the housing such that the first touch control and the second touch control are configured to be simultaneously activated with a pinching motion of a hand of the patient. The first touch control and the second touch control may each be disposed proximate or within a respective depression within the respective surface of the housing to guide the finger of the patient toward the respective touch control.

In some implementations, the first threshold level of force is in a range from 400 g-f to 1000 g-f. The second threshold level of force may be in a range from 80 g-f to 400 g-f. A differential between the first threshold level of force and the second threshold level of force may be at least 100 g-f.

In some implementations, delaying the treatment includes delaying the treatment responsive to detecting actuation of the force-activated switch of the second touch control along with application of the force value at the first touch control.

In some implementations, analyzing the first signal includes analyzing a first time-series of signals from the force sensor of the first touch control to identify the force value as a force applied over a threshold period of time.

In some implementations, the second touch control includes a second force sensor, and monitoring the signals from the first touch control and the second touch control includes analyzing a third signal from the second force sensor. The monitoring may include, responsive to detecting application of a second force value below the first threshold level of force and at or above the second threshold level of force to the second touch control along with application of the force value to the first touch control, delaying the treatment. The first touch control may include a second force-activated switch, and the method may further include delaying, by the at least one processor, the treatment responsive to, over the predetermined period of time, detecting application of a second force value below the first threshold level of force and at or above the second threshold level of force to the second touch control along with actuation of the force-activated switch of the first touch control. The second threshold level of force may be less than or equal to a force required for actuation of the second force-activated switch.

In some implementations, the method further includes delaying, by the at least one processor, the treatment responsive to, over the predetermined period of time, detecting actuation of the second touch control along with continuous application of force below the first threshold level of force and at or above the second threshold level of force to the first touch control for a threshold period of time.

In some implementations, the method further includes delaying, by the at least one processor, the treatment responsive to, over the predetermined period of time, detecting actuation of the second touch control along with intermittent application of force below the first threshold level of force and at or above the second threshold level of force to the first touch control over a threshold window of time. The intermittent application of force may occur at least every 60 seconds. The threshold window of time may be between 15 to 60 seconds.

In some implementations, the method further includes, prior to detecting the indication of the cardiac anomaly, conducting, by the at least one processor, a calibration sequence including detecting actuation of one of the first touch control and the second touch control along with application of at least the threshold force to the other of the first touch control and the second touch control, after the detecting, monitoring signals from the first touch control and the second touch control over a calibration period of time to determine an activation profile of the patient, and storing at least one of the activation profile and an identification of an activation threshold force in a non-transitory computer readable memory. Detecting the application of below the first threshold level of force and at or above the second threshold level of force to the first touch control may include detecting the application of at least the below the first threshold level of force and at or above the second threshold level of force based in part on the at least one of the activation profile and the identification of the activation threshold force. Conducting the calibration sequence may include repeating the detecting, the monitoring, and the storing, and determining the at least one of the activation profile and the identification of an activation threshold force based upon data obtained through the repeating.

In some implementations, at least one of the first threshold level of force and the second threshold level of force is determined based on calibration data obtained through a calibration exercise with the patient. The method may further include periodically initiating, by the at least one processor, the calibration exercise. The method may further include conducting, by the at least one processor, a calibration sequence outside the calibration exercise and during routine user interaction with the control unit in order to determine typical force applied to the first touch control; and adjusting, by the at least one processor, at least one of the first threshold level of force and the second threshold level of force based on the calibration sequence.

In some implementations, the method further includes adjusting, by the at least one processor, at least one of the first threshold level of force and the second threshold level of force based on signals received from at least one of an accelerometer, a gyroscope, and a magnetometer in communication with the control unit.

In some implementations, the method further includes releasably affixing the wearable medical device to a torso of the patient using an adhesive.

In one aspect, the present disclosure relates to a wearable medical device for providing electrical therapy to a patient responsive to monitoring the patient, the wearable medical device including a number of monitoring sensors configured to be in electrical communication with a body of the patient, a number of therapy electrodes configured to provide electrical therapy to the patient, and a control unit in communication with the number of monitoring sensors and the number of therapy electrodes. The control unit may include a housing, and two or more buttons each configured to be contacted with a finger of the patient, the two or more buttons including a first button including a first force sensor and a first force-activated switch, where the first force sensor is configured to register and signal application of forces upon the first button insufficient to activate the first force-activated switch, and a second button including a second force sensor and a second force-activated switch, where the second force sensor is configured to register and signal application of forces upon the second button insufficient to activate the second force-activated switch. The wearable medical device may include monitoring circuitry in communication with the number of monitoring sensors and the two or more buttons, a non-transitory computer-readable memory in communication with the monitoring circuitry, and at least one processor in communication with the non-transitory computer-readable memory and the monitoring circuitry. The at least one processor may be configured to detect, via the number of monitoring sensors, indication of a cardiac anomaly, provide the patient with a notification, after providing the notification, monitor, over a predetermined period of time, signals from the first button and the second button to identify a patient response to the notification. The monitoring may include detecting both a) at least one of actuation of the first button and application of at least a first threshold force to the first button, and b) at least one of actuation of the second button and application of at least a second threshold force to the second button, where the first threshold force is less than a force level required to actuate the first force-activated switch, and the second threshold force is less than a force level required to actuate the second force-activated switch. The at least one processor may be configured to, responsive to the detecting, register the patient response.

In some implementations, the first button is disposed on a first surface of the housing, and the second button is disposed on a second surface of the housing. The first surface may be opposite the second surface of the housing such that the first button and the second button are configured to be simultaneously activated with a pinching motion of a hand of the patient. The first button and the second button may each be disposed proximate or within a respective depression within the respective surface of the housing to guide the finger of the patient toward the respective button.

In some implementations, the first threshold force is in a range from 400 g-f to 1000 g-f. The second threshold force may be in a range from 80 g-f to 400 g-f. A differential between the first threshold force and the second threshold force may be at least 100 g-f.

In some implementations, the at least one processor is configured to, after registering the response, delay the electrical therapy.

In some implementations, detecting application of one or more of the at least the first threshold force and the at least the second threshold force includes analyzing a first time-series of signals from a force sensor of the respective button to identify a force value as forces applied over a threshold period of time. Each of the first button and the second button may include a respective force sensor.

In some implementations, detecting application of one or more of the at least the first threshold force and the at least the second threshold force includes detecting continuous application of force at or above the respective first threshold force or second threshold force to the respective first button or second button for a threshold period of time.

In some implementations, detecting application of one or more of the at least the first threshold force and the at least the second threshold force includes detecting intermittent application of force at or above the respective first threshold force or second threshold force to the respective first button or second button over a threshold window of time. The intermittent application of force may occur at least every 60 seconds. The threshold window of time may be between 15 to 60 seconds.

In some implementations, the at least one processor is configured to, prior to detecting the indication of the cardiac anomaly, conduct a calibration sequence including detecting actuation of one of the first button and the second button along with application of at least the respective threshold force to the other of the first button and the second button, after the detecting, monitoring signals from the first button and the second button over a calibration period of time to determine an activation profile of the patient, and storing at least one of the activation profile and an identification of an activation threshold force in the non-transitory computer readable memory. Detecting application of one or more of the at least the first threshold force and the at least the second threshold force may include detecting the application of the respective threshold force based in part on the at least one of the activation profile and the identification of the activation threshold force. Conducting the calibration sequence may include repeating the detecting, the monitoring, and the storing, and determining the at least one of the activation profile and the identification of an activation threshold force based upon data obtained through the repeating.

In some implementations, at least one of the first threshold level of force and the second threshold level of force is determined based on calibration data obtained through a calibration exercise with the patient. The at least one processor may be configured to periodically initiate the calibration exercise. The at least one processor may be configured to conduct a calibration sequence outside the calibration exercise and during routine user interaction with the control unit in order to determine typical force applied to the first button and the second button, and adjust at least one of the first threshold level of force and the second threshold level of force based on the calibration sequence.

In some implementations, the at least one processor is configured to adjust at least one of the first threshold level of force and the second threshold level of force based on signals received from at least one of an accelerometer, a gyroscope, and a magnetometer in communication with the control unit.

In some implementations, the wearable medical device is releasably affixed to a torso of the patient using an adhesive.

In one aspect, the present disclosure relates to a method for providing electrical therapy to a patient responsive to monitoring the patient, the method including receiving, by monitoring circuitry in communication with a number of monitoring sensors in electrical communication with a body of the patient, sensor data, using the sensor data, detecting, by at least one processor, indication of a cardiac anomaly, providing, by the at least one processor, the patient with a notification, and, after providing the notification, monitoring, by the at least one processor over a predetermined period of time, signals from two or more buttons each configured to be contacted with a finger of the patient to identify a patient response to the notification. The two or more buttons may include a first button including a first force sensor and a first force-activated switch, where the first force sensor is configured to register and signal application of forces upon the first button insufficient to activate the first force-activated switch, and a second button including a second force sensor and a second force-activated switch, where the second force sensor is configured to register and signal application of forces upon the second button insufficient to activate the second force-activated switch. The signals may be provided by the monitoring circuitry. The monitoring may include detecting both a) at least one of actuation of the first button and application of at least a first threshold force to the first button, and b) at least one of actuation of the second button and application of at least a second threshold force to the second button, where the first threshold force is less than a force level required to actuate the first force-activated switch, and the second threshold force is less than a force level required to actuate the second force-activated switch. The method may include, responsive to the detecting, registering, by the at least one processor, the patient response.

In some implementations, a control unit includes the at least one processor, where the first button is disposed on a first surface of a housing of the control unit, and the second button is disposed on a second surface of the housing. The first surface may be opposite the second surface of the housing such that the first button and the second button are configured to be simultaneously activated with a pinching motion of a hand of the patient. The first button and the second button may each be disposed proximate or within a respective depression within the respective surface of the housing to guide the finger of the patient toward the respective button.

In some implementations, the first threshold force is in a range from 80 g-f to 400 g-f. The force level required to actuate the first force-activated switch may be in a range from 400 g-f to 1000 g-f.

In some implementations, the method further includes, after registering the response, delaying, by the at least one processor, the electrical therapy.

In some implementations, detecting application of one or more of the at least the first threshold force and the at least the second threshold force includes analyzing a first time-series of signals from a force sensor of the respective button to identify a force value as forces applied over a threshold period of time.

In some implementations, each of the first button and the second button includes a respective force sensor.

In some implementations, detecting application of one or more of the at least the first threshold force and the at least the second threshold force includes detecting continuous application of force at or above the respective first threshold force or second threshold force to the respective first button or second button for a threshold period of time.

In some implementations, detecting application of one or more of the at least the first threshold force and the at least the second threshold force includes detecting intermittent application of force at or above the respective first threshold force or second threshold force to the respective first button or second button over a threshold window of time. The intermittent application of force may occur at least every 60 seconds. The window of time may be between 15 to 60 seconds.

In some implementations, the method further includes, prior to detecting the indication of the cardiac anomaly, conducting, by the at least one processor, a calibration sequence including detecting actuation of one of the first button and the second button along with application of at least the respective threshold force to the other of the first button and the second button, after the detecting, monitoring signals from the first button and the second button over a calibration period of time to determine an activation profile of the patient, and storing at least one of the activation profile and an identification of an activation threshold force in the non-transitory computer readable memory. Detecting application of one or more of the at least the first threshold force and the at least the second threshold force may include detecting the application of the respective threshold force based in part on the at least one of the activation profile and the identification of the activation threshold force. Conducting the calibration sequence may include repeating the detecting, the monitoring, and the storing, and determining the at least one of the activation profile and the identification of an activation threshold force based upon data obtained through the repeating.

In some implementations, at least one of the first threshold level of force and the second threshold level of force is determined based on calibration data obtained through a calibration exercise with the patient. The method may further include periodically initiating, by the at least one processor, the calibration exercise. The method may further include conducting, by the at least one processor, a calibration sequence outside the calibration exercise and during routine user interaction with the control unit in order to determine typical force applied to the first button and the second button, and adjusting, by the at least one processor, at least one of the first threshold level of force and the second threshold level of force based on the calibration sequence.

In some implementations, the method further includes adjusting, by the at least one processor, at least one of the first threshold level of force and the second threshold level of force based on signals received from at least one of an accelerometer, a gyroscope, and a magnetometer in communication with the control unit.

In some implementations, the method further includes releasably affixing the wearable medical device to a torso of the patient using an adhesive.

In one aspect, the present disclosure relates to a wearable medical device including a number of ECG sensors configured to be in electrical contact with a body of a patient, a number of therapy electrodes configured to provide electrical therapy to a heart of the patient, and a control unit connected to the number of ECG sensors and the number of therapy electrodes. The control unit may include a housing, and at least one touch control disposed on the housing, where the at least one touch control is configured to be contacted with a finger of the patient, and the at least one touch control includes a force sensor. The wearable medical device may include a memory, and a processor in communication with the memory. The processor may be configured to monitor, over a predetermined period of time, for a user input based on signals from the at least one touch control, where the monitoring includes analyzing a first signal from the at least one touch control to identify application of a user force at the force sensor, determining that a force value of the user force is in a range from a lower predetermined force threshold to an upper predetermined force threshold, and responsive to detecting application of the user force in the range, register the user input.

In some implementations, analyzing the first signal includes analyzing a first time-series of signals from the force sensor of the at least one touch control to identify the force value as a force applied over a threshold period of time. The processor may be configured to, prior to monitoring for the user input, provide the patient with a notification regarding commencement of a treatment. Monitoring for the user input may include, after registering the user input, verifying the user input is to activate a failsafe override of the treatment, and upon the verifying, delaying the treatment. Verifying user input is to activate the failsafe override of the treatment may include analyzing, over a second predetermined period of time, a number of signals from the at least one touch control, identifying, from the number of signals, at least one of a) a pulsed force persisting throughout the second predetermined period of time, each pulse of the pulsed force in the range from the lower predetermined force threshold to the upper predetermined force threshold, and b) a predetermined pattern of applied forces, each force of the predetermined pattern of applied forces in the range from the lower predetermined force threshold to the upper predetermined force threshold, and, upon the identifying, delaying the treatment.

In some implementations, the lower predetermined force threshold is about 80 g-f and the upper predetermined force threshold is about 400 g-f. The upper threshold level of force may be configured to be less than or equal to a force required for actuation of a force-activated switch of the at least one touch control.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples. The figures are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1A:
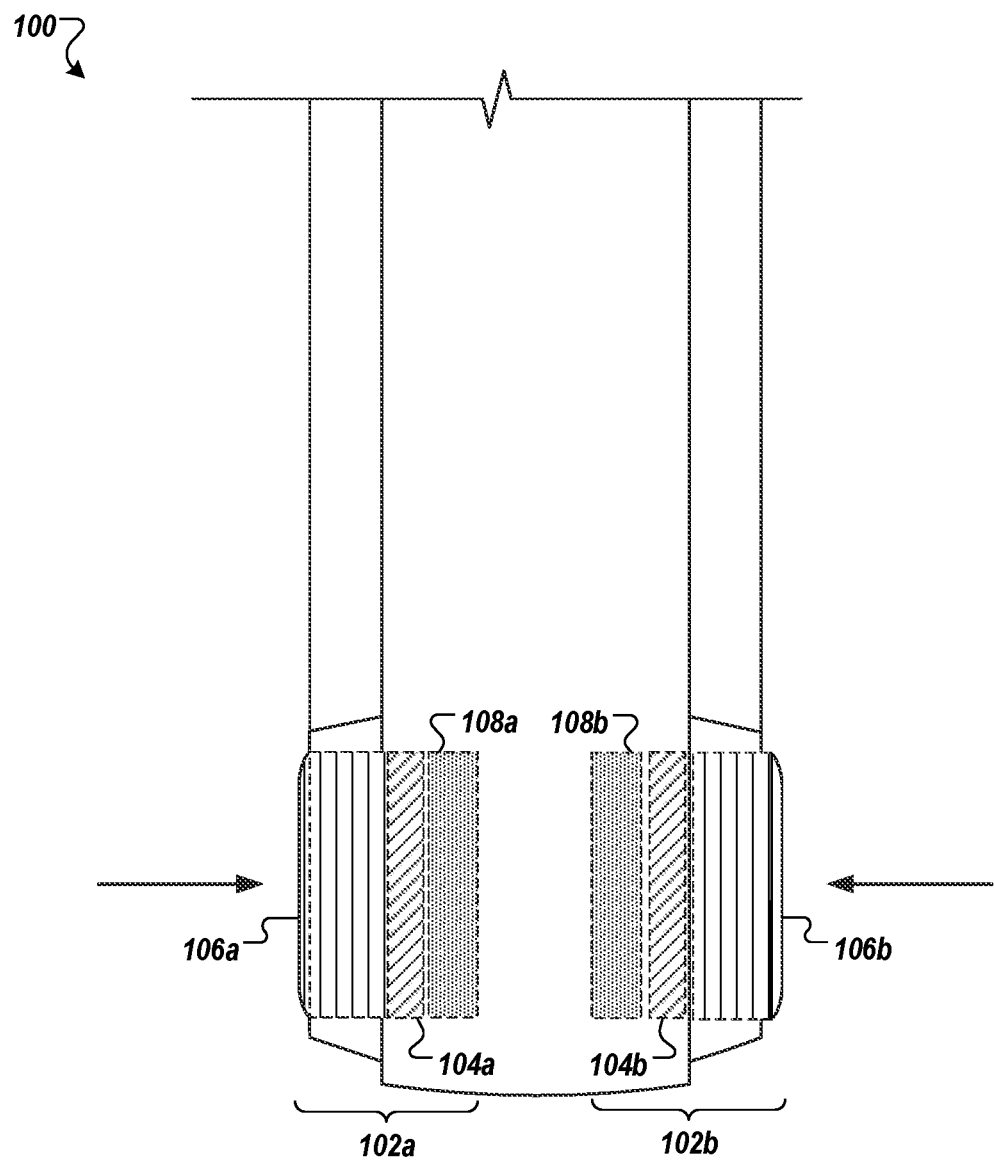
FIG. 1A depicts an example combination force-activated switch control and force sensor.

Various resuscitation efforts aim to maintain the body's circulatory and respiratory systems during cardiac arrest in an attempt to save the life of the patient. The sooner these resuscitation efforts begin, the better the patient's chances of survival.

Example external cardiac monitoring and/or treatment devices include cardiac monitors such as the ZOLL Cardiac Monitor, the ZOLL LifeVest® wearable cardioverter defibrillator, and the AED Plus, all available from ZOLL Medical Corporation (Chelmsford, MA).

This disclosure relates to failsafe methods, systems, and apparatus for a wearable health monitoring device such as a cardiac monitor. The response mechanisms described herein are configured for use by a user of the device such as the patient wearing the device or, in some scenarios, the patient's caregiver. The failsafe methods, systems, and apparatus endeavor to register inputs to the wearable health monitoring device likely to be indicative of intentional interaction with the wearable health monitoring device as opposed to, for example, unintentional actuation of control apparatus. The failsafe methods, systems, and apparatus may be customized, in some examples, to the capabilities or dexterity of a certain patient or a target patient population. This can allow the medical device to be responsive to patients who, in some examples, lack full strength and motor skills or who have a neurological disorder or other medical concern which can complicate interactions with the user controls of the medical device. Upon receiving signals from various user interface controls, in some examples, circuitry and/or algorithms of a controller of the medical device may be designed to verify that forces applied to the controls meet preprogrammed conditions or thresholds for registering user input.

Touch controls or switches (e.g., response buttons) used for patient feedback during operation of a medical device, such as the response buttons provided in a traditional wearable cardioverter defibrillator (WCD), may offer one force level for registering a patient's interaction with the touch control or switch, such as an interaction indicating desire to delay treatment or an interaction indicating positive response to a query posed to the patient through a user interface of the medical device. In an illustrative example, a WCD may use a set of switches (for example, dome switches, membrane switches, scissor switches, capacitive switches, swing switches, Hall-effect switches, among others) each requiring an equivalent of about 0.88 lbf of actuation force for patient activation. For patients with normal strength, the current actuation force of the response buttons offers assurance that a response is accurate and desired by the patient. Patients with joint pain, weakness, or other degradation of fine motor control, on the other hand, may exhibit a reduced ability to actuate existing touch controls. In implementations described herein, a dependable failsafe solution for patient response can assist the aforementioned patient population with actuating the touch controls. For example, the touch controls may include both switches as described above as well as force sensors. Further, in some implementations described herein, the failsafe solution for patient response may include overriding therapeutic delivery.

The addition of a force sensor to one or more response buttons of the medical device can allow the medical device controller (e.g., control unit) or wearable medical device interface pod to recognize and monitor a wider range of forces applied to each response button than in a traditional WCD. Even when the patient is incapable of applying sufficient force to actuate the switch, the force sensor will provide signals to the medical device controller indicative of movement of the response button. In an illustrative example, an appropriate force sensor's sensitivity may range from 10 gram-force (0.022 lbf) to 1000 gram-force (2.20 lbf) applied to each response button. The controller may then be configured to use signals from the force sensor(s) to determine whether the use has attempted to actuate the response button(s).

Although described herein as the ability to identify with confidence a failsafe override of therapeutic delivery by the medical device, conversely, the same teachings may be equally applied to identifying failsafe user or patient responses for a variety of other device actions upon receipt of touch inputs to a controller. The user may be asked to provide input in response to a prompt by the device. The user's response may be registered using the failsafe patient response as described herein. For example, the patient may be asked a question about the patient's current state of health. Question(s) can include "did you sleep more than 8 hours last night?" or "are you experiencing one or more of the following symptoms: shortness of breath, chest pain, and skipped beat?". The device may prompt for a user (such as the patient's caregiver) or the patient itself to confirm whether the patient would like for the device to record an ECG strip for storage to a memory on the device. In response to these questions and/or prompts, the user or the patient can press the response buttons and the response can be registered using the failsafe mechanisms described herein.

FIG. 1A depicts example touch controls 102a,b having a combination force-activated switch control and force sensor for use in a touch control interface 100 of a medical device. The touch control interface 100, for example, may be part of a portable controller such as the controller 230 of FIGS. 2C and 2D. As illustrated, the combination force-activated switch control and force sensor touch controls 102a,b include, for each side of the touch control interface 100, a push button style touch control 106a,b over a force sensor 104a,b. This dual touch control layout, for example, may be used to avoid errant inputs to the controller caused by, in some examples, depression of a single touch control 102a,b while leaning against a surface or upon falling. In other examples, a similar goal may be achieved through a single combination force-activated switch control and force sensor. In further examples, one side may include the combination force-activated switch control and force sensor, while the other side may include a force-activated switch control without a corresponding force sensor. Other combinations are possible.

In operation, upon depression of the dome-shaped buttons 106a,b, a force is applied to the each of the force sensors 104a, 104b positioned beneath the respective dome-shaped button 106a,b. The force to the buttons 106a,b may be applied by the user at the same time or consecutively, depending upon implementation, to indicate intentional activation of the touch controls. The force applied by a user to the buttons 106a,b, in some circumstances, may not be great enough to actuate a force-activated switch 108a,b of the touch control 102a,b but instead is only registered by the force sensor 104a,b. In this scenario, a controller may analyze signals from the force sensors 104a,b to determine whether sufficient force has been applied to each of the force sensors 104a,b to register activation by the user. In other circumstances, the user may apply an adequate force to one of the buttons 106a,b to actuate the force-activated switch 108a,b but only enough force to the other of the buttons 106a,b to trigger a signal from the corresponding force sensor 104a,b. In this scenario, a controller may analyze the signal from the one force sensor 104a,b to determine whether the user applied sufficient force to register activation of the two touch controls 102a,b by the user. In the illustrative example, for example, button 106a is partially depressed, such that it is contacting force sensor 104a but has not yet exerted force upon 108a to cause the force-activated switch to activate. Conversely, button 106b is in a fully disengaged state, being separated from the force sensor 104b. Finally, in the circumstance where the user successfully actuates both force-activated switch 108a,b, analysis may not be needed to accept register user input to the controller.

While illustrated as having dome-shaped buttons 106a,b, in other implementations, the force-activated switch includes a flat or recessed button. Substituting flat or recessed buttons, for example, may reduce the likelihood of errant inputs to the controller through depression of the buttons 106a,b by objects, pets, or other actors pushing against the surface of the controller. The buttons, in some examples, are designed for ease of location by the user. For example, recessed buttons may be easier for the user to feel for than a flat surface. Dome-shaped buttons, however, may be easy to locate while providing greater tactile indication of engagement due to the surface of the push button applying force to the fingerprint of the user.

Although illustrated as including a switch-activated push button 106a,b and force sensor 104a,b for each touch control interface, in other implementations, one or both of the touch controls 102a,b may be implemented using a button interface overlaying a force sensor without a force-activated switch. In this circumstance, the controller would be reliant upon hardware and/or software analysis of signals from the force sensor regardless of force applied by the user. This design may be simpler and more stream-lined (less bulky) than the design described above. However, having a back-up mechanism of the force-activated switches 108a,b in the circumstance of force sensor failure may be useful in some implementations. In other implementations, multiple force sensors may supply such failsafe mechanism without reliance upon the force-activated switch 108a,b.

In some implementations, the force sensor 108a,b is a variable-resistive device having a first film layer with suspended, embedded conductive particles designed to act as a path for current flow and a second film layer having conductive wire traces thereon. The first film layer may have a normally high resistance, but when a force is applied that depresses the first film layer, a large number of embedded conductive particles are pushed into contact with each other, lowering the material's resistance. Thus, the first film layer may have a variable, decreasing resistance with a downward force applied to it. The first film layer, for example, will return to its original resistance when released. The second film layer may hold a conductive copper interleaving of opposing finger traces. In operation, the finger traces do not change their resistance with a downward force is applied. Instead, the finger traces contact the first film layer to bridge the circuit with the conductive particles of the first film layer, carrying the current through the first film layer. By applying a greater depressive force through pressing down with a finger, a greater number of the embedded particles come into contact with the finger traces and with neighboring conductive particles, reducing the measurable resistance at the opposing finger traces.

Figure 1B:
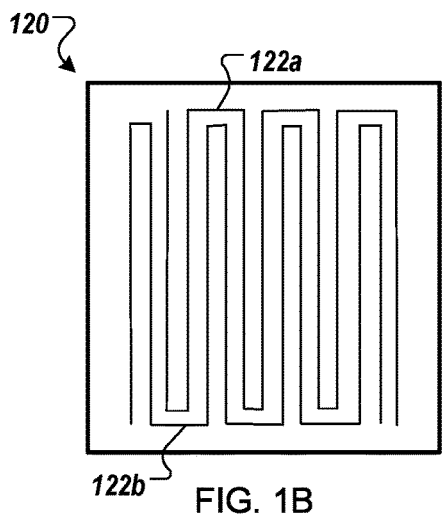
FIGS. 1B-1D depict example resistive force sensors.

FIG. 1B illustrates a simplified example of a variable-resistive force sensing device. As illustrated in FIG. 1B, two interleaving finger traces 122a and 122b are illustrated within a body of a force sensor 120. Although illustrated as a rectangular layout, in other examples, the force sensor 120 may be oval-shaped or circular. The shape of the force sensor 120, in some implementations, is selected in part to better match a surface area of the overlying button interface of the touch control.

Returning to FIG. 1A, the force sensor 104a,b, in some implementations, is a piezo-resistive device having two conductive layers with force-sensitive piezo-resistive ink. The output signal responsive to application of force is proportional to the force and thus linear. The piezo-resistive device, therefor has a large range of detection couple with simplicity of electronics for detecting forces. Further, piezo-resistive devices are generally low in power consumption and have a very small footprint.

In some implementations, the force sensor 104a,b outputs a variable resistance signal usable in determining voltage thresholds which correspond to applied force. In one example, a voltage follower circuit accepts outputs of the variable-resistive force sensor and thresholds the output to identify forces corresponding to predetermined force levels or force within a predetermined range of force (e.g., indicative of intentional application of force upon the touch control). In illustration, a variable voltage divider can create a voltage based upon the output variable resistance. Thresholding, then, may be performed by a comparator circuit positioned at the output of the variable voltage divider. The predetermined force levels, in one example, relate to threshold forces applied to each force sensor. For example, two or more comparators (e.g., non-inverting, inverting, and/or window comparator) can be deployed within the comparator circuit to detect multiple present voltage levels in determining applied forces within a predetermined range. In another example, combinations of predetermined force levels applied to two or more force sensors (e.g., at least X application at a first force sensor along with at least Y application of force at a second force sensor) are combined in the comparator circuit to identify forces corresponding to predetermined force levels. The predetermined force levels, in some examples, are statically defined. For example, one or more predetermined force levels, or thresholds, may be hardcoded into the hardware and/or software of the controller unit. In other examples, the predetermined force levels are adjustable. For example, the predetermined force levels may be customized to correspond to the strength of an individual user based upon test forces applied to the response button(s) during an initialization or set-up routine. In one example, software selectable resistors can be used to refine the threshold force levels.

In some implementations, the comparator circuit includes a timing component to ensure the patient is applying a force for at least a predetermined period of time. In one example, software-selectable resistors can be used to measure output over time. Depending on the implementation, various aspects of timing may be of interest. In a first example, duration of signal at or above a threshold value for a predetermined period of time may be indicative of a purposeful patient input, as compared to an errant voltage spike or an unintentional depression of a response button. In another example, variable input force, such as increasing force over time, may be indicative of depression of the response button by the patient's finger as opposed to a force imposed by an object pressing against the response button. In a third example, a pulsed force may be indicative of the muscle spasms or tremors in a patient with a known health condition that inhibits ability to produce a sustained force upon the response button. The pulsed force, for example, may involve pulses of force of at least a threshold force value registered intermittently over time, separated by variable periods in which lower force(s) than the threshold force value are registered and/or no force activity is registered.

Multiple force sensors, in some implementations, are deployed in parallel to increase sensitivity of the force level thresholding. For example, two or more variable-resistive force sensors may be stacked for increased sensitivity. Additionally, simpler and lower cost force sensors can be used in parallel to supply more consistent results in signal output. In some examples, signals from each force sensor are added to produce a total force value. The total force value, for example, may be thresholded using the predetermined force level(s) discussed above. In another example, two or more variable-resistive force sensors may be stacked to reduce error conditions (e.g., transient signals not directly generated through force applied to the response button(s)). In a third example, a force sensor suspected of producing errant outputs may be automatically swapped out of the circuit (e.g., its outputs no longer considered in identifying purposeful patient inputs) while another force sensor may be swapped into its place to ensure reliability of outcome. Further to the example, in examples using three or more force sensors in parallel, the outputs of two or more remaining force sensors may be used to increase sensitivity and/or reduce error conditions as discussed above.

In some implementations, multiple force sensors are disposed beneath the button interface of the touch control in a horizontally adjacent fashion. Application of force by a patient's finger should be spread out upon each response button and thus spread across any force sensor(s) disposed beneath the touch interface. In positioning multiple force sensors adjacently beneath the touch control button interface, therefore, the effect of transient signals may be reduced by ensuring two or more signals exist prior to registering force applied by a patient. In one example, the output signals of the two or more force sensors may be AND combined to ensure contemporaneous signals detected across the force sensor surface. In another example, the signals from each of the two or more force sensors may be provided to a controller for analysis and determination of subsequent action. The force sensors may be variable-resistive force sensors.

Figure 1C:
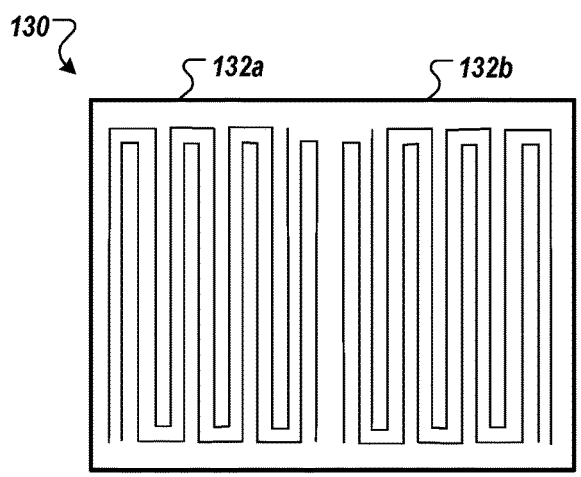

In some implementations, two or more force sensors are deployed side-by-side, as illustrated in FIG. 1C. Turning to FIG. 1C, a first force sensor 132*a* is positioned adjacent to a second force sensor 13*b*. Although pictured as having its finger traces disposed upon a same shared surface, in other examples, two or more fully separate force sensors may be deployed. Other layouts are possible, such as a grid or stripes of force sensors. Additionally, although illustrated as a rectangular force sensor, other shapes such as circular or oval are possible, as discussed above.

Figure 1D:
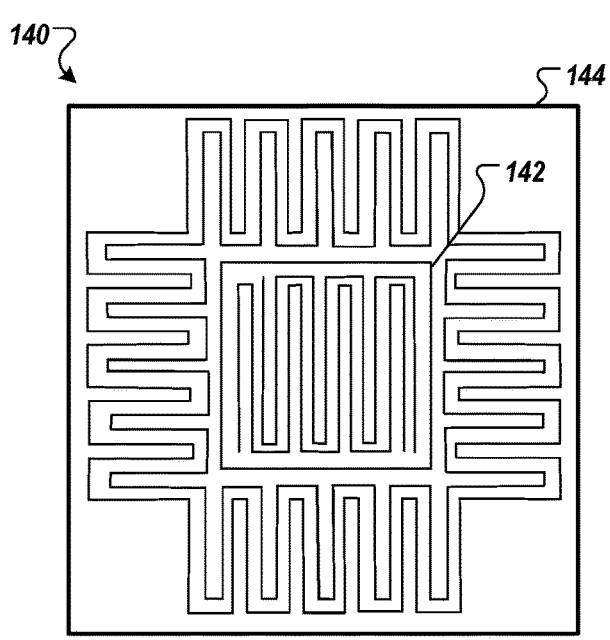

In some implementations, the multiple force sensors may be presented in concentric rings, beneath the touch contact of the response button. As illustrated in FIG. 1D, a simplified diagram of concentrically disposed force sensors illustrates an inner box 142 including a first set of finger traces and an outer box 144 including a second set of finger traces. Three or more force sensors may be disposed in a similar fashion. Further, although illustrated as being physically separated by a bounding box, in other examples, two or more force sensors may be deposited within a single force sensor body. Additionally, although illustrated as a rectangular force sensor, other shapes such as circular or oval are possible, as discussed above.

In implementations, a force sensor associated with a button or a touch control can include either a single sensor element or multiple sensor elements disposed in series and/or in parallel for registering forces applied to the button or touch control. For example, each force sensor as described herein may include a plurality of sensor elements arranged within an array. Outputs from each element within such an array can be combined in a predetermined manner. For example, the outputs from the plurality of elements may be averaged or summed to provide a composite response as the output value associated with the force sensor. Other methods of combining the outputs of individual sensor elements to form a force sensor output are possible.

As indicated above, signals from the force sensor(s) 104*a*, 104*b*, in some examples, are analyzed by a processor in the control unit of a medical device to determine whether a patient intends to activate the touch control(s) 102*a,b*. For example, the touch controls 102*a*, 102*b* may be used as a failsafe mechanism for the medical device. To override medical treatment, in a first example, the patient may be instructed to depress one or more of the buttons 106*a*, 106*b* in a manner indicative of an intentional input by the patient (e.g., simultaneously, repeatedly, for a threshold period of time, etc.). In a second example, the touch controls 102*a*, 102*b* may be used as a mechanism to activate medical treatment. Similar to overriding, activation of medical treatment, such as a TENS treatment or pharmaceutical release, may require the patient to demonstrate intentional input through applying force(s) to the touch control(s). In a third example, the touch controls 102*a*, 102*b* may be used by the patient to provide input in response to a device prompt. Further, the touch controls 102*a*, 102*b* may be used alone or in combination with one or more additional touch controls or input mechanisms to interact with features of a controller, such as the controllers described in relation to FIGS. 2A through 2E. In one example, the touch controls 102*a*, 102*b* may be used to activate a user interface session during which the user may interact with user interface features of the controller, such as settings. In another example, the touch controls 102*a,b* may be used to activate a patient monitoring session during which the medical device collects information, such as sensor data, indicative of the health of the patient for sharing with medical professionals.

When user input is expected, the processor will monitor for the user input in a manner described above during a predetermined period of time. For example, the predetermined period of time may be set via a user-configurable parameter specifying an amount of time for the patient to respond to a prompt or query requiring a response. In certain implementations, to seek the user's response in a failsafe matter, the device may, after registering the initial user input, prompt the patient to provide a second user input. The processor will then monitor for the second user input in the manner described above during a second predetermined period of time. For example, the second predetermined period of time may also be set via a user-configurable parameter specifying an amount of time for the patient to respond. For example, the predetermined period of time may be set to a default value of between 5 to 30 seconds. For example, the second predetermined period of time may be set to a default value of between 5 to 30 seconds.

Where a cardiac anomaly needs to be treated is detected, in some implementations, the predetermined period of time may be set to a default value of between 30 to 60 seconds during which the patient's response is required to avoid shock delivery. The second predetermined period of time may be set also to a default value of a further 30 to 60 seconds during which the patient's confirmatory response is required to avoid shock delivery.

Figure 4:
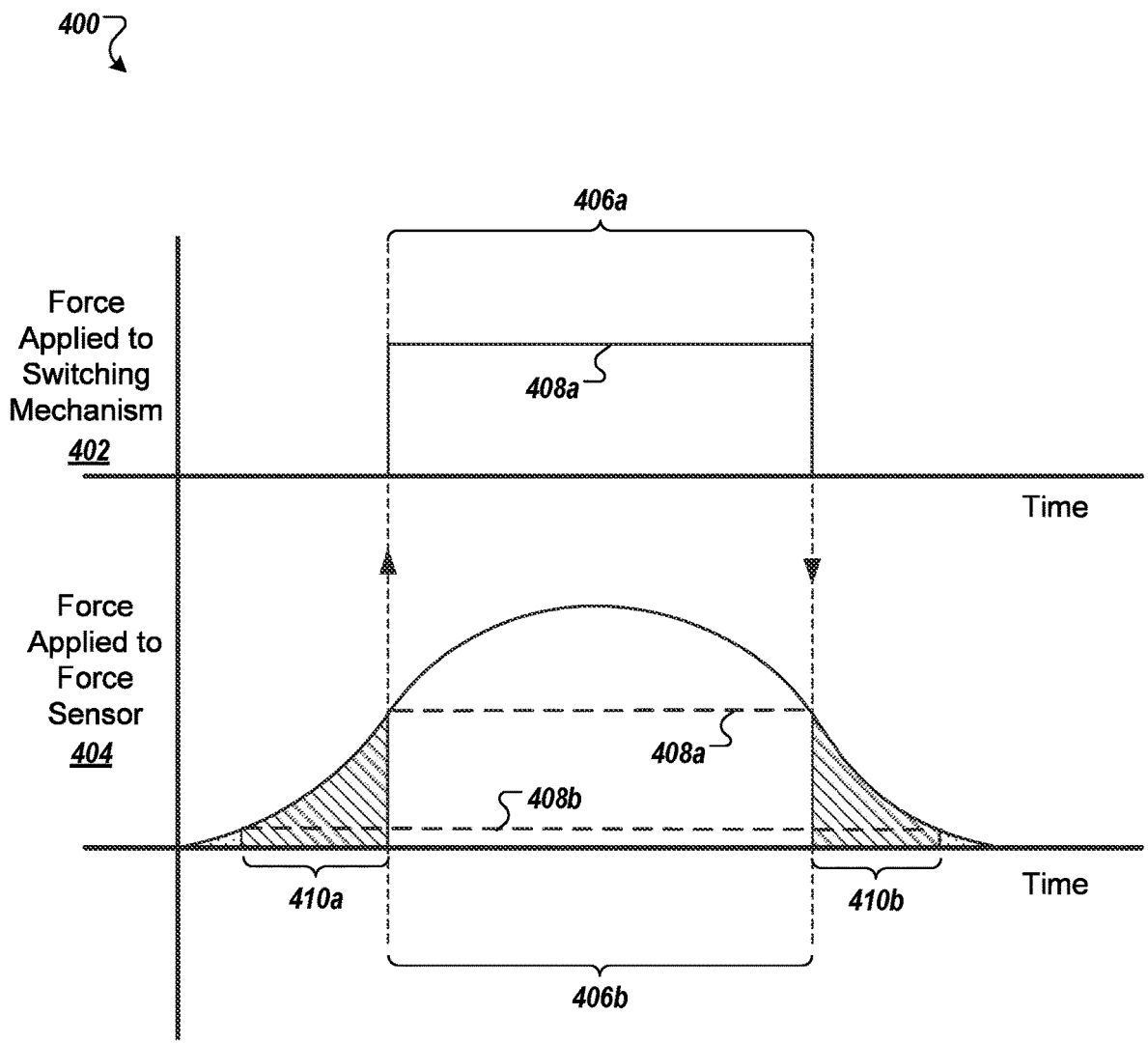
FIG. 4 illustrates a graphical example of forces applied to the combination force-activated switch control and force sensor of FIG. 1 with resultant signal effects.

FIG. 4 illustrates a graph 400 charting example forces applied to a touch control with a combination force-activated switch and force sensor, such as the touch controls 102*a*, 102*b* of FIG. 1, with resultant signal effects. The X axis graphs both an output signal curve of the force sensor in an upper region 402 as well as an effect upon the force-activated switch responsive to forces applied to the touch control in a lower region 404. The Y axis graphs force applied to the touch control interface (e.g., button). The graph, for example, may map signal outputs of both the force-activated switch and the force sensor in response to the gradual application, followed by gradual removal, of force by a user upon the touch control.

As illustrated in FIG. 4, a range of forces can be applied to a combination force-activated switch and force sensor to indicate user activation. In a first example, when adequate force $F_1$ 408a has been applied to the touch control to actuate the force-activated switch as illustrated in region 406a, a corresponding first predetermined threshold force $F_1$ 408a or above, as illustrated in a region 406b, may be registered via signals from the force sensor. The controller, in this circumstance, may react to either the closing of the switch or the force of at least $F_1$ 408a as indication of an input to the touch control. In another example, when the force applied does not actuate the force-activated switch, as illustrated in regions 410a and 410b, signals from the force sensor may be applied to determining whether the force is indicative of user activation. For example, hardware and/or software may determine whether a force applied to the touch control meets or exceeds a second predetermined force threshold $F_2$ 408b (e.g., is within a range from $F_2$ 408b to $F_1$ 408a).

In some examples, the processor analyzes signals from the force sensor to register a response from the patient based on one or more traits of the patient as follows. For example, the device can be programmed to set the second threshold force $F_2$ 408b, in some examples, in part based upon patient demographics such as age and gender. In some examples, the device can be programmed to set the second threshold force $F_2$ 408b in part based upon a known health disorder of the patient using the medical device. In some examples, arthritis, Parkinson's disease, multiple sclerosis, spinal injury, or stroke may cause loss of coordination or dexterity which can affect a patient's ability to grasp and hold down touch controls. The device can be programmed to set the second threshold to compensate for a patient with a known condition that can adversely affect grasp strength or dexterity. In further examples, the device can be programmed to set the second threshold force $F_2$ 408b such that it is customized for a certain patient through a setup routine for the medical device designed to obtain forces applied to the touch controls by the patient.

In some implementations, two force-activated switches with integrated force sensors are monitored for combined signal behavior indicative of intentional activation. The following table illustrates possible combinations of switch actuation and force sensor measurements that may be used for the determination of whether to register the patient's response, e.g., in some implementations, to register the patient's response to delay medical treatment. Switch 1 and force sensor 1 belong to a first touch control, while switch 2 and force sensor 2 belong to a second touch control. The values indicated in the chart below, in one illustration, may correspond to the first predetermined threshold force $F_1$ 408a for the switch (e.g., 400 g-f) and the second predetermined threshold force $F_2$ 408b for the force sensor (e.g., 100 g-f). Although illustrated as certain force references or thresholds, in further examples, combinations may include force ranges of forces. In an illustrative example in relation to Force Sensor 1, actionable forces may be in a range of 100 g-f<=$F_{sensor1}$<400 g-f.

In some examples, the second predetermined threshold may be described as a range of force values between a lower predetermined force threshold and an upper predetermined force threshold. In this regard, the range of actionable forces for the first predetermined threshold may be between about 400 g-f and 1000 g-f, between about 400 g-f and 2000 g-f, or between about 400 g-f and 3000 g-f. If a user force therefore exceeds 400 g-f and goes up to 1000 g-f, 2000 g-f, or even 3000 g-f, the processor will determine register the input. On the other hand, a range of actionable forces for a second predetermined threshold may be between a lower predetermined force threshold of around 5 g-f and an upper predetermined force threshold of around 400 g-f, between about 80 g-f and 350 g-f. Table 1 illustrates a range of actionable forces between around 100 g-f and around 400 g-f as in Table 1.

TABLE 1

Chart of Force Combinations to Register Patient Response

| Switch 1 | Force Sensor 1 | Force Sensor 2 | Switch 2 | Patient response registered? |
|---|---|---|---|---|
| | | | | No |
| | | | 400g-f or greater | No |
| | | 100g-f | | No |
| | | 100g-f | 400g-f or greater | No |
| | 100g-f | | | No |
| | 100g-f | | 400g-f or greater | Yes |
| | 100g-f | 100g-f | | Yes |
| | 100g-f | 100g-f | 400g-f or greater | Yes |
| 400g-f or greater | | | | No |
| 400g-f or greater | | | 400g-f or greater | Yes |
| 400g-f or greater | | 100g-f | | Yes |
| 400g-f or greater | | 100g-f | 400g-f or greater | Yes |
| 400g-f or greater | 100g-f | | | No |
| 400g-f or greater | 100g-f | | 400g-f or greater | Yes |
| 400g-f or greater | 100g-f | 100g-f | | Yes |
| 400g-f or greater | 100g-f | 100g-f | 400g-f or greater | Yes |
| | 50g-f+ pulses | | 400g-f or greater | Yes |
| 400g-f or greater | | 50g-f+ pulses | | Yes |
| | 50g-f+ pulses | 50g-f+ pulses | | Yes |

As illustrated in the table above, in some examples, any combination of threshold forces applied to both of the first touch control and the second touch control may be adequate to trigger delay of medical treatment. These combinations include actuation of both of the switch 1 and switch 2, actuation of one of the switch 1 or switch 2 in combination with threshold force applied to the force sensor of the other of the switch one or switch 2, as well as threshold force applied to the force sensors of both of the touch controls without actuation of either of switch 1 or switch 2.

In some examples, the threshold force may differ between touch controls. For example, depending upon positioning, the anticipated application of force upon each touch control may differ (e.g., a thumb press may be stronger than an index finger press. In another example, if the patient has a known impairment that effects movement of the thumb differently than movement of the index finger, the touch control situated for actuation by the patient's thumb may be set with a different force threshold than the touch control situated for actuation by the patient's index finger. The force differential between touch controls, in some examples, may range from 0 g-f to 50 g-f or from 0 to 20 g-f.

Additionally, as illustrated in the final three rows of Table 1, in some implementations, identification of repeated, pulsed forces upon one or both of the force sensors can supplant or enhance determination of delay of medical treatment. A repeated pulsed force, for example, may be indicative of a health disorder in the patient resulting in a tremor that inhibits the patient from applying a stronger, sustained force to the touch control. The pulsed force, for example, may involve pulses of force of at least a threshold force value (e.g., forces within a range from $F_2$ 408b to $F_1$ 408a) registered intermittently over time, separated by variable periods in which lower force(s) than the threshold force value are registered and/or no force activity is registered. As illustrated, the threshold pulsed force (at least 50 g-f) is lower than the sustained force of 100 g-f. In other examples, these threshold forces may be the same or closer in value.

To register the patient's response, in some implementations, the forces and/or switch actuations are measured over time to ensure at least a threshold period of time of touch control activation. The time period, for example, may be set to avoid misinterpretation of errant signals output by the force sensor(s). In another example, the time period may be set to avoid acceptance of accidental contacting of the touch controls, for example by a pet jumping in the patient's lap or a small child reaching over and briefly playing with the controller. For example, the threshold period of time may be set to a default value of 0.5 seconds. The threshold period of time may be a user-configurable value that may be set within a range of about 0.3 seconds to about 2 seconds. In the circumstance of the repeated pulsed force (e.g., forces registered at variable intervals), in some examples, a threshold number of pulses (e.g., at least 5 pulses within one second), an average interval between pulses (e.g., up to about 0.5 seconds average interval between pulses), or a pulse pattern generally matching a previously stored activation profile of the patient (e.g., typical forces applied by the patient, typical periods between forces applied by the patient, and/or typical ramping, releasing of forces applied by the patient, etc.) may be substituted or added to the threshold period of time.

In some examples, the processor is configured to, after registering the user input, verify the user input to confirm that the user intended the user input. For example, the processor can verify the user input by requesting that the patient provide, during a second predetermined period of time, a second user input. For instance, the control unit can include a microphone that receives a voice input provided by the patient. The microphone and associated circuitry can transform the voice input into an electrical signal indicating the voice input from the patient. The processor can analyze the electrical signal to determine whether the voice input is one of expected voice inputs. For instance, the circuitry can include voice synthesizer circuitry for determining one or more speech characteristics of the patient thereby recognizing the patient or other designated user's voice. In this manner, the processor can verify the user input on receiving a voice input from the patient confirming the user input.

In some implementations, the second user input can include application of a second user force at the force sensor at or above the first predetermined force threshold during the second predetermined period of time. The second user input can also include application of the second user force at the force sensor at or above the second predetermined force threshold and below the first predetermined force threshold during the second predetermined period of time.

In some implementations, the second user input can include a pulsed force persisting throughout the second predetermined period of time. For example, each pulse of the pulsed force may be at or exceeding the second predetermined force threshold. The second user input can also include a predetermined pattern of applied forces. For example, each force of the predetermined pattern of applied forces may be at or exceeding the second predetermined force threshold.

In some implementations, forces applied to both of the first touch control and the second touch control are analyzed as a function of the individual forces received to determine whether to register the received forces as patient activation of the controls and, thus, adequate to trigger delay of medical treatment. In one example, patient actuation of two touch controls on opposite sides of a control unit (e.g., "pinching") may involve similar forces applied to both touch controls, while patient actuation of two touch controls on a same side of a control unit may involve disparate forces depending upon relative strengths between fingers of the patient's hand. For this reason, different combined forces may be reviewed using different mathematical functions depending, in some examples, upon the medical device implementation and/or patient capabilities to apply force to the various touch controls. In some examples, two or more functions are performed in parallel or in series to verify patient activation of the touch controls. Further, in some examples, the forces may first be individually analyzed as described above to establish base registration of application of force upon each touch control, then analyzed using one or more mathematical functions, in combination, to verify patient activation of the touch controls.

In a first example, the threshold force required to register patient activation of the touch controls may be a function of differences in forces (e.g., $|F_1-F_2|$) to ensure that the force applied to the first touch control is within a threshold differential of the force applied to the second touch control. The threshold differential for verifying patient activation, in some examples, may be between 0 and 50 g-f, between 0 and 35 g-f, or between 0 and 20 g-f.

In a second example, the threshold force required to register patient activation of the touch controls may be a function of a summation of the forces, such as a direct summation function (e.g., $F_1+F_2$) or an average function (e.g., $(F_1+F_2)/2$). In illustration, if the predetermined threshold value to register patient interaction with the touch controls is set to 100 g-f of average force, a first force $F_1$=80 g-f is sensed at the first touch control, and a second force $F_2$=120 g-f is sensed at the second touch control, then the average of 100 g-f meets the threshold average force for registering the patient input as being indicative of an intentional actuation of the controls. In another illustration, if the predetermined threshold value to register patient interaction with the touch controls is set to 200 g-f of total force, a first force $F_1$=80 g-f is sensed at the first touch control, and a second force $F_2$=120 g-f is sensed at the second touch control, then the sum of 80 g-f+120 g-f=200 g-f meets the threshold, thus causing the device to register the patient's input as being indicative of an intentional actuation of the touch controls.

In further examples, the threshold force required to register patient activation of the touch controls may involve application of a logarithm function, an exponential function, a complex function, or another predetermined mathematical function.

FIGS. 2A through 2D illustrate a variety of control units for a medical device, each including at least one touch control with force sensor.

The force sensor, in some examples, provides a failsafe mechanism for application of therapy by the medical device. In one example, one or more response buttons of the ZOLL LifeVest® wearable cardioverter defibrillator may include a force sensor to increase assurance of recognition of depression of the response button(s) to avoid delivery of defibrillating shock treatment to an alert patient.

The touch controls, in some examples, are used by the patient to interface with the control unit for reasons beyond the failsafe mechanism. In one example, one or more response buttons may be depressed to initiate interaction with the controller of the medical device. For example, depression of one or more touch controls may cause the user interface (e.g., graphical screen, voice interaction system, etc.) to exit sleep mode and engage with the patient. In another example, the response button(s) may be depressed to ensure proper battery functionality upon battery replacement. The response button(s), in a further example, may be depressed to capture a time period of health measurements for physician review. For example, the response button(s) may be held for a threshold length of time to initiate recording of the patient's heart rhythm.

Figure 2B:
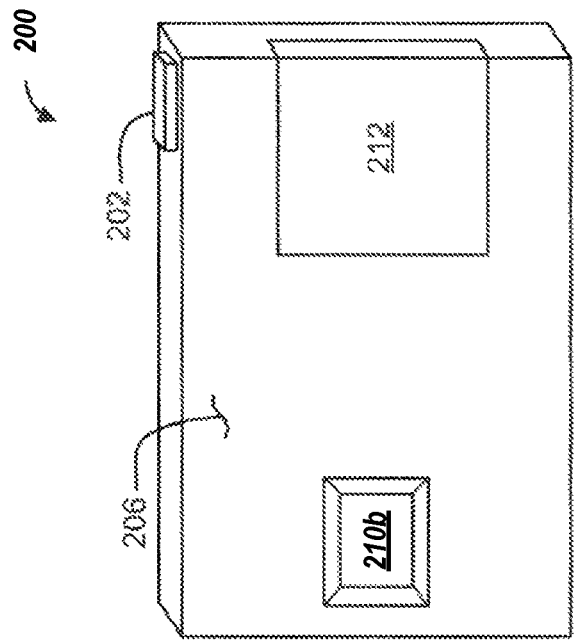
FIG. 2B depicts an opposite side of the first example control unit with a second touch control.
Figure 2A:
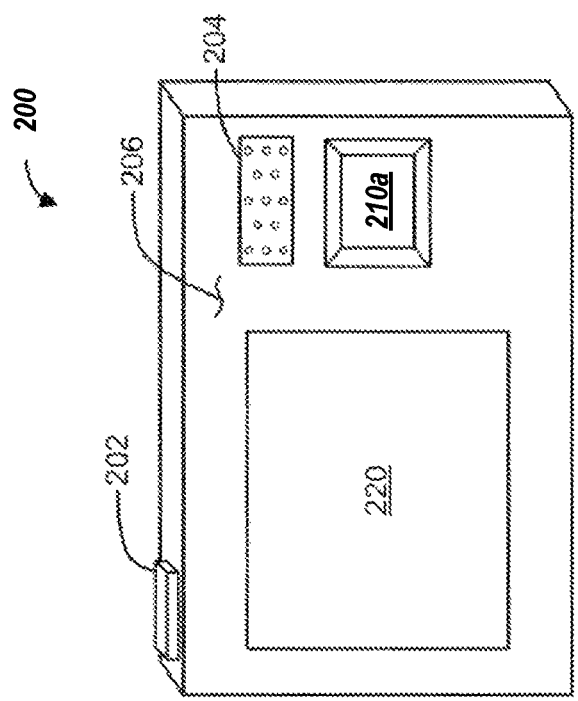
FIG. 2A depicts a first example control unit with a single touch control disposed on a surface thereof for actuation using a patient's finger.

FIG. 2A depicts a first example control unit 200 with a single touch control 210 disposed on a surface of a housing 206 for actuation using a patient's finger. The control unit 200 may be designed as a control interface for supplying information to a medical device connected to or otherwise in communication with the control unit 200, such as settings information, treatment delay instructions, and/or treatment activation instructions. Further, the control unit 200 may supply power to the medical device using a battery included in the control unit 200. Additionally, the control unit 200 may receive monitoring signals representing health measurements gathered by the medical device. The control unit 200 is designed to analyze the monitoring signals gathered by the medical device for indications of cardiac anomalies in the patient. In some examples, the control unit 200 is designed to provide monitoring signals to an external computing system, such as to a portable computing device maintained for at least a portion of use of the medical device in proximity to the control unit 200 by the patient, or to a network-based computing system via a wireless network connection.

In some implementations, the control unit 200 includes a port 202 to removably connect medical equipment. In one example, the medical device may be connected to the control unit 200 via the port 202. The medical device, for example, may include ECG sensing electrodes to detect cardiac arrhythmia and therapy electrodes for supplying defibrillating shocks responsive to such detection. In another example, peripheral sensing devices to the medical device, such as, in some examples, a wearable neuromodulator, a wearable physical activity monitoring device, or a wearable mental activity monitoring device, may be connected to the control unit 200 via the port 202.

The control unit 200, in some examples, includes output features for providing information to the patient, caregiver, and/or bystanders. The control unit 200 may include a video screen 220 to output visual information. The video screen 220, in some implementations, includes touch input capability such that the patient and/or caregiver can interact with the video screen 220 to control a medical device connected to or otherwise in communication with the control unit 200. The control unit 200 may include a speaker 204 for communicating audio information to the patient, caregiver, and/or the bystander. The information provided upon the video screen 220 and/or via the speaker 204 may include a warning indication alerting the patient that a medical treatment is about to commence. In an illustrative example, the warning indication may relay to the patient, caregiver, and/or bystanders that, according to data collected by the medical device, the patient is experiencing cardiac arrhythmia. Further, the warning indication may also instruct the patient to press and hold one or more response buttons 210 on the control unit 200 to indicate that the patient is conscious, thereby triggering the control unit 200 to instruct the medical device to withhold the delivery of one or more therapeutic defibrillating shocks. If the patient does not respond to an instruction from the control unit 200, the control unit 200 may determine that the patient is unconscious and allow the medical device to proceed with the treatment sequence, culminating in the delivery of one or more defibrillating shocks to the body of the patient.

The single touch control 210a, as described previously, may include both a force-activated switch and a force sensor for registering user response. In other examples, the single touch control 210a may include a force sensor but no force-activated switch. The single touch control 210a, in comparison to the dual touch controls discussed above, may be more accessible for a patient lacking full functionality of grasping, for example due to physical or neurological conditions specific to the patient. However, the single response button 210a can be more prone to erroneous input than relying upon indications received from at least two touch controls.

In some implementations, a portion of the touch analysis related to the force sensor is hardware-based and built into the circuitry of the touch control 210a. In some examples, the touch control 210a includes thresholding circuitry. For example, as discussed above in relation to touch controls, a variable resistance force sensor may supply outputs to a voltage follower circuit that thresholds the output to register forces corresponding to predetermined force levels indicative of intentional application of force upon the touch control. A software component of the control unit 200 may receive signals from the thresholding circuitry to determine a response related to user activation of the touch control 210a.

In some implementations, the single touch control 210a is positioned upon the control unit to avoid unintentional actuation of the touch control 210a. For example, the single touch control 210a may be positioned within a recessed area or on a surface unlikely to be contacted upon falling or leaning against furniture. In another example, a shield may be positioned over the button surface such that the patient needs to reach in to access the touch control 210a.

The control unit, in some implementations, is programmed to monitor signals from the force sensor and the force-activated switch of the single touch control 210a and identify a pattern of force application indicative of intentional actuation of the single touch control. The pattern, for example, may include a series of two or more purposeful actuations of the single touch control 210a or force applications sensed by a force sensor as having a threshold force or above indicative of an intentional activation of the single touch control 210a. The pattern, in some examples, includes a temporal aspect. For example, the pattern may include both one or more "long" presses of the touch control 210a causing indication of an actuated switch or force upon the force sensor for at least a first threshold period of time, as well as one or more "short" presses of the touch control 210a causing indication of an actuated switch or force upon the force sensor for at least a second threshold period of time substantially shorter than the first threshold period of time. In an illustrative example, the pattern may include a "long" press, followed by a "short" press, followed by a "long" press, where the "long" press is at least 0.8 seconds long and the short press is between 0.25 and 0.5 seconds long. The "long" press may similarly have an upper threshold time period to avoid identifying force from an inanimate object as an intentional press. For example, the "long" press may range from 0.8 seconds to 1.5 seconds.

In some examples, the control unit 200 is programmed to cue the patient to follow a pattern of force activation to ensure intentional actuation of the single touch control 210a. In a first example, an audible cue emitted from the speaker 204 may direct the patient to enter a pattern of touches to the touch control 210a. In a second example, a visual cue emitted from the video screen 220 or another visible indicator, such as an LED, presented on a surface more visibly accessible to the patient if wearing the control unit 200 on a belt (e.g., on the same surface as the port 202) may direct the patient in entering the pattern of touches. Combinations are also possible. For example, an audible indication instructing the user to "press the response button each time the screen turns green" followed by a series of green screens temporally separated by non-green screens could be used to guide the patient through presses of the touch control 210a. In another example involving a touch control having tactile feedback capability, a message provided through the speaker 204 or screen 220 may alert the patient to place their finger on the touch control 210a and press down whenever the touch control 210a vibrates.

Although entry of patterns of presses are described in relation to individual presses, in other examples, patterns of periods of pulsing (e.g., forces registered at variable intervals) may be substituted for patterns of more stable force asserted upon the touch control 210a. As discussed above in relation to FIG. 4, for example, a patient with a tremor may still interface with the touch control 210a to enter a pattern, but each individual touch entry of the pattern may be recognized as pulsing rather than a press of less variable force.

In an implementation of the single touch control 210a, the control unit 200 can be programmed to monitor for a first input (e.g., a first touch or button press) during a first predetermined time period when an input is expected and register the patient's response when the first touch or button press has ended. For example, if an arrhythmia is occurring, the device can prompt the patient to press the touch control 210a. The control unit 200 can then monitor for the first input for, e.g., 60 seconds after delivering the prompt. To register as the first input, the control unit 200 can monitor for a predetermined amount of force and/or a predetermined pattern of pulsed forces as described above (e.g., see Table 1) being applied on the single touch control 210a. When the first input has been received in such manner, the control unit 200 monitors for when the patient has ended the first input after the 60 seconds window. If the first input has not ended, for instance, if the patient has lost consciousness and fallen in a manner that continues to depress the touch control 210a, the device audibly and/or visual prompts the patient to release the button. The device may use a combination of verbal instructions, audible sirens or gongs, or other alarm methods to prompt the patient. The control unit 200 provides the patient with an additional second predetermined time period (e.g., 60 seconds) to release the button. If the first touch or button press has still not ended, the device can proceed to deliver the therapy. The above scheme can be varied in accordance with the patient's specific preferences. For example, the first and second predetermined time periods can be adjusted to account for the patient's typical response times. Along these lines, examples timing schemes for prompting the patient to release the single touch control 210a or otherwise proceeding to treatment are described in application Ser. No. 14/318,186, titled "Systems and methods of delivering therapy using an ambulatory medical device," filed Jun. 27, 2014 (issued on Feb. 28, 2017 as U.S. Pat. No. 9,579,516) which is incorporated by reference herein in its entirety.

Turning to FIG. 2B, in some implementations, the control unit 200 includes a second touch control 210b on an opposite surface to the first touch control 210a. In some examples, the control unit 200 is configurable to accept a failsafe override input using a single button rather than two buttons while physically housing two buttons. For example, based upon an individual patient's physical abilities, the control unit 200 may be set up (e.g., through software settings) to accept failsafe override inputs (or, conversely, therapy activation inputs) by pressing only one of the two touch controls 210a, 210b. In other examples, the control unit 200 relies upon inputs to both touch controls 210a,b for failsafe override of the medical device. These examples, for example, may follow a structure similar to the touch control input logic illustrated in the graph 400 of FIG. 4. The patient may enter a failsafe override, in some examples, by simultaneously pressing both the first touch control 210a and the second touch control 210b by "pinching" the control unit 200.

In some examples, the second touch control 210b includes a force-activated switch and a force sensor, as described above in relation to FIG. 1. In other examples, the second touch control 210b includes one of these features (e.g., either a force sensor or a force-activated switch).

In some implementations, the two touch controls 210a,b share at least a portion of the thresholding circuitry. For simplicity of design, weight reduction, and heat reduction, in some examples, the thresholding circuitry may receive inputs from both the first touch control 210a and the second touch control 210b. In one example, software-selected resistors for semi-customizable thresholding may be shared between the first touch control 210a and the second touch control 210b. In other implementations, the thresholding circuitry for the first touch control 210a is separate from the thresholding circuitry for the second touch control 210b. This may lead to faster responsiveness of the circuitry.

As described in relation to FIG. 2A, a patient may be visually and/or audibly instructed by the control unit 200 to press both the first touch control 210a and the second touch control 210b to enact a failsafe override of therapy by the medical device. In some examples, rather than instructing certain presses, the medical device simply alerts that therapy will be delivered soon. Patient training regarding overriding may be relied upon, in this circumstance, rather than specific instruction regarding pressing. This may ensure that a bystander will not override necessary treatment through being instructed by the control unit 200 on how to do so.

As illustrated in FIG. 2B, in some implementations, the control unit 200 is powered by a rechargeable battery accessible via a battery port 212. The rechargeable battery may be removable from the housing 206 of the control unit 200 to enable a patient and/or caregiver to swap a depleted (or near depleted) battery for a charged battery.

Figures 2C, 2D:
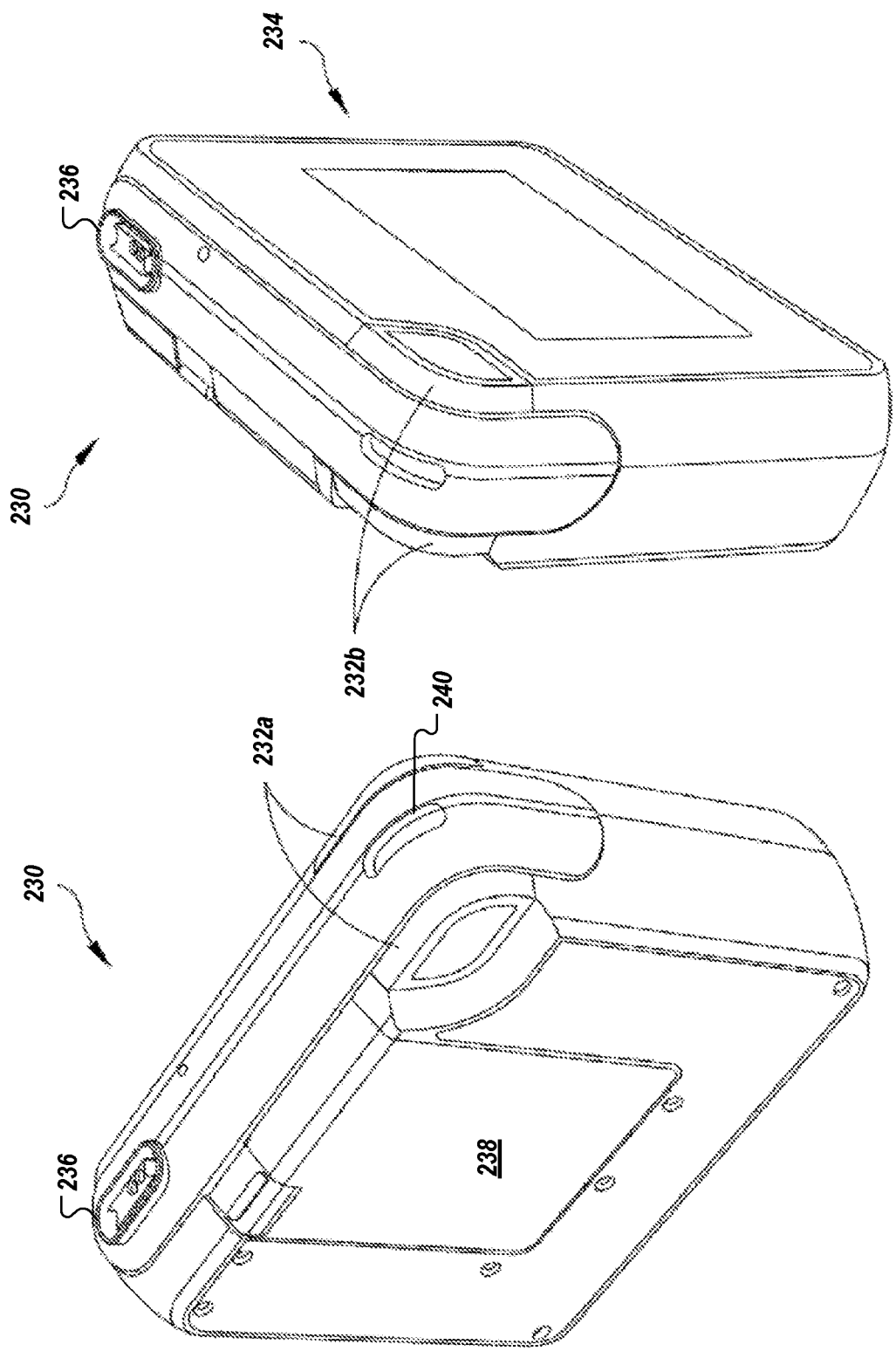
FIGS. 2C and 2D illustrate a second example control unit with touch controls disposed on opposing surfaces for pinch actuation using a patient's finger and thumb.

In some implementations, the controls are positioned upon the control unit to avoid unintentional actuation of the touch controls. FIGS. 2C and 2D depict a second example control unit 230 with two touch controls 232a,b disposed on opposing surfaces for pinch actuation using a patient's finger and thumb, similar to the design of FIGS. 2A-B. As shown in FIGS. 2C-D, the touch controls 232 are recessed below a plane of an outer surface of the housing to reduce the likelihood of accidental activation (e.g., a patient falling on and actuating the response button).

The positioning of the touch controls 232a,b toward a top region of the control unit 230 may aid in actuation by allowing easier access by the left or the right hand of the patient. Thus, if the patient has numbness or other temporary difficulty in using a certain hand, the patient may find it easier to engage the touch controls 232a,b in the upper positioning than the positioning illustrated in FIGS. 2A and 2B of the touch controls 210.

In some examples, the control unit 230 includes a display screen 234 to enable the communication of visual information to the patient, such as the display screen 220 of FIG. 2A. In addition, the display screen 234 may also incorporate a touch screen interface to enable the patient to interact with control unit 230.

The control unit 230, in some implementations, includes a number of similar features as the control unit 200 of FIGS. 2A-B. For example, the control unit 232 includes a port 236, similar to the port 202, for connecting a medical device or other periphery device to the control unit 230. Further, the control unit 230 includes a battery port 238, similar to the battery port 212. Finally, the control unit 230 includes a speaker 240, similar to the speaker 204.

In other examples, rather than being placed on opposing sides of the housing as illustrated in FIGS. 2C-D, the touch controls may be positioned on a same surface or on perpendicular surfaces. The touch controls, for example, may be located adjacent to each other in the housing of the control unit. The adjacent placement of the touch controls may make it easier for individuals with smaller hands or less dexterity to engage the touch controls.

Figure 2E:
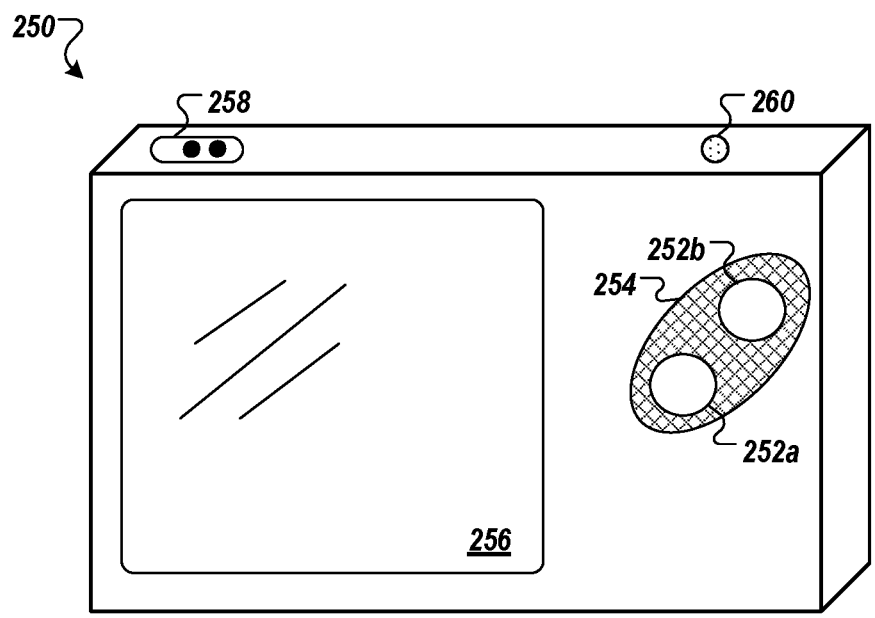
FIG. 2E depicts a third example control unit with touch controls disposed on a same surface for actuation using a patient's two fingers.

FIG. 2E depicts a third example control unit 250 with multiple touch controls 252a,b disposed on a same surface for actuation using a patient's two fingers. The touch controls 252a,b, as illustrated, are positioned within a recessed region 254 of a front face of the control unit 250. The touch controls 252a,b, in some examples, are offset in alignment to provide ergonomic placement of the patient's index and middle fingers for manipulating the touch controls 252a,b. In other examples, the touch controls 252a,b may be vertically aligned for side access or horizontally aligned for access from the top (e.g., with the patient's palm resting on a top surface of the control unit 250). Other alignments are possible. As discussed in relation to the control unit 200 of FIGS. 2A-B, one or both of the touch controls 252a,b may include a force sensor for identifying attempts to press a button surface of the touch control without actual actuation of a switch.

Since co-location of the two touch controls 252a,b can possibly result in inadvertent depression of both of the touch controls (e.g., by falling against something that presses into the recess 254), in some implementations, the control unit 250 is configured to require a more elaborate indication of intentional interaction with the touch controls 252a,b. Similar to the discussion related to control unit 210 of FIG. 2A in the single touch control configuration, multiple presses upon the touch controls 252a, 252b and/or consecutive touches to the touch controls 252a, 252b separated by up to a threshold period of time may be required to identify intentional pressing by the patient.

In some examples, the control unit 250 includes a visible indicator 260 (e.g., surface mounted light emitting diode (LED) or other illuminating feature) for cuing the patient in following a touch pattern. The visible indicator 260, for example, may illuminate when the user should depress one or more of the touch controls 252. Although illustrated as being positioned on a top surface of the control unit 250, to avoid the user overlapping the visible indicator 260 with a thumb or palm, in other examples the visible indicator 260 may be positioned on an opposite end (e.g., closer to a port 258 for connecting the medical device or other peripheral equipment to the control unit 250). In further examples, rather than having a separate visible indicator 260, the patient may be prompted via a display screen 256.

Figure 3A:
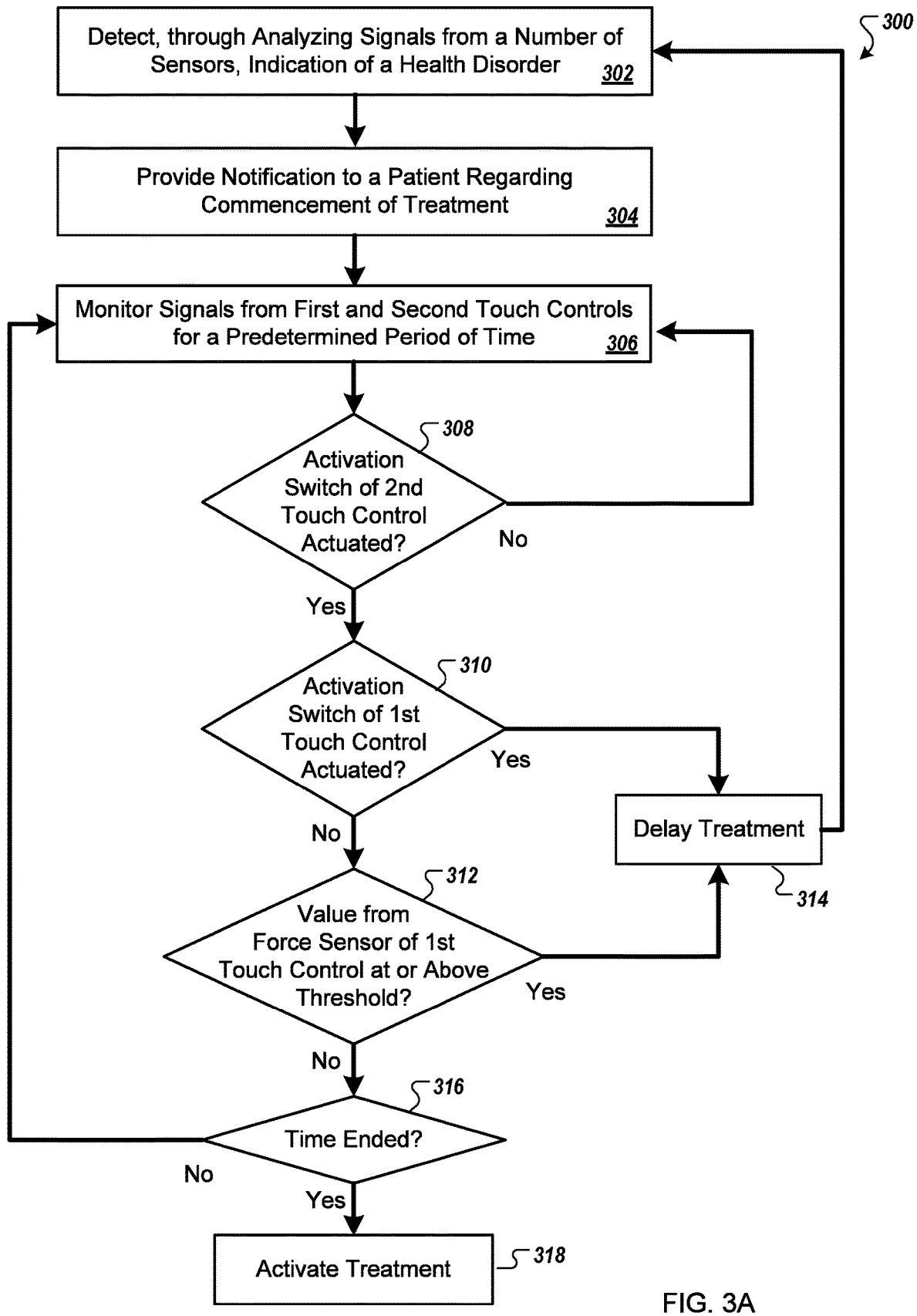
FIG. 3A is a flow chart of an example method for failsafe delay of therapy delivery through signal monitoring of two touch controls, one having a force sensor.

FIG. 3A is a flow chart of an example method 300 for failsafe delay of therapy delivery through signal monitoring of two touch controls, one having a force sensor. The method 300 includes a number of steps that can be performed by one or more components of a medical device, such as the medical device 600 of FIG. 6, including, in some examples, a computing device or system in communication with the medical device, such as a remote (e.g., cloud-based) computing system or portable computing device. In illustrative examples, the steps of the method 300 may be performed by the control unit 620 of the medical device 600 (or, similarly, control unit 200 of FIG. 2A, control unit 230 of FIG. 2C, or control unit 250 of FIG. 2E), by the control unit of the medical device in combination with a remote computing system, or by a separate computing system or device such as a portable computing device in communication with the medical device.

In some implementations, the process 300 begins with detecting indication of a cardiac anomaly through analyzing signals from a number of sensors (302). The sensors, in some examples, include a number of skin-facing electrodes of a medical device, such as the medical device 600 of FIG. 6. The cardiac anomaly, for example, may be cardiac arrhythmias such as ventricular tachycardia or ventricular fibrillation that may be treated by defibrillation pulses, or bradycardia (e.g., can be programmed to be set at less than 30 beats per minute) or tachycardia (e.g., can be programmed to be set at more than 150 beats per minute) that may be treated by pacing pulses. The determination of whether the outcome of the analysis is indicative of likelihood of cardiac anomaly, in some examples, is based on a comparison of the patient's current cardiac data/morphology template (e.g., QRS complex) to their baseline morphology template. In another example, basic metrics may be applied to irregularity index/indices to determine whether ECG data is beyond a certain threshold.

In some implementations, a notification is provided to a patient regarding commencement of treatment (304). For example, upon failure of the current cardiac data/morphology template to substantially match the baseline morphology template or upon determining that the ECG data is beyond the threshold, a notification may be provided to the patient. For example, the patient may be alerted regarding commencement of treatment via a verbal message or shrill alarm produced by the patient interface pod 640 of the medical device 600 of FIG. 6 and/or the speaker of the control unit. Examples of notifications issued by the control unit are described in application Ser. No. 13/428,703, titled "SYSTEM AND METHOD FOR ADAPTING ALARMS IN A WEARABLE MEDICAL DEVICE," filed Mar. 23, 2012 (issued on Sep. 15, 2015 as U.S. Pat. No. 9,135,398) which is incorporated by reference herein in its entirety. The patient may also be instructed to press and hold one or more buttons on the control unit or on the user interface pod of the medical device to indicate that the patient is conscious, thereby instructing the control unit or medical device to withhold the delivery of one or more therapeutic defibrillating shocks.

In some implementations, signals are monitored from first and second touch controls over a predetermined window of time (306). The signals, for example, may include signals from at least one force sensor such as the force sensors 104a,b of FIG. 1A. Further, in some examples, the signals may include signals from at least one force-activated switch. The second touch control includes a touch interface (e.g., button) and a force-activated switch. The second touch control includes a touch interface (e.g., button), a force sensor and a force-activated switch.

If the force-activated switch of the second touch control is actuated (308), in some implementations, the method 300 determines whether the force-activated switch of the first touch control is actuated (310) or a value from a force sensor of the first touch control is at or above a threshold value (312). For example, the value from the force sensor may be in a range from a lower threshold value to an upper threshold value (e.g., near or at the actuation force of the force-activated switch). In this manner, the method 300 endeavors to determine whether purposeful activations of both the first and the second touch control have been received. They may be received simultaneously or consecutively, depending upon example and/or user activation practice.

If, after actuation of the force-activated switch of the second touch control, signal(s) are received from the first touch control indicating actuation of the force-activated switch of the first touch control (310), in some implementations, therapeutic treatment is delayed (314). For example, while a defibrillating shock may not be delivered to the patient, the medical device will continue to monitor the sensor data for further evidence of ongoing cardiac anomaly and, upon substantial evidence (302), may re-initiate the notification (304).

Conversely, if, after actuation of the force-activated switch of the second touch control, signals are received from the first touch control indicating forces applied to the force sensor at or above a threshold value (312), in some implementations, therapeutic treatment is delayed (314). The threshold value, in some examples, may be 80 gram-force, 100 gram-force, 200 gram-force, or 300 gram-force. In an example, the threshold value may be within a range of 80 gram-force to 400 gram-force.

To avoid errant signal outputs of the force sensor being recognized as patient inputs, in some examples, the signals are monitored for sustained signal activity of at least a threshold period of time. For example, a force sensor may output a brief signal within a range that would otherwise be indicative of a purposeful force applied to the touch control due to an errant electrical circumstance unrelated to force applied to the sensor. To avoid acting upon such signals, the signals may be monitored for sustained signal activity. The threshold period of time, in some examples, may be at least 0.3 seconds, at least 0.5 seconds, or at least 1 second. Although described as "sustained" it should be understood that the signals over time likely follow a ramping and diminishing force curve, such as the curve in the lower region 404 of the graph 400, which follows the depression and release of the touch control by the patient. For example, the forces applied during the threshold period of time may be within the range from the lower threshold value to the activation force of the force-activated switch. In some examples, the forces applied during the threshold period of time may briefly exceed the activation force of the force-activated switch.

In some examples, the threshold value is selected for the patient wearing the medical device. A threshold may be selected to compensate for a patient with a known condition that can adversely effect grasp strength or dexterity, such as arthritis or Parkinson's disease. In another example, the predetermined force levels may be customized to correspond to the strength of an individual user based upon test forces applied to the response button(s) during an initialization or set-up routine.

If, instead, the predetermined window of time passes without simultaneous or successive registrations of activation of both the first touch control and the second touch control (316), in some implementations, therapeutic treatment is activated (318). If the patient does not respond, the patient may be presumed to be unconscious. Thus, the treatment sequence may proceed, for example culminating in the delivery of one or more defibrillating shocks to the body of the patient.

Although illustrated in a certain series of steps, in other examples, more or fewer steps may be included in the method 300. For example, in further examples, once activation of the force-activated switch of the second touch control has been identified, the method 300 may begin a timer for receipt of signals from the second touch control (310, 312). For example, the patient may need to provide inputs to both the first touch control and the second touch control within a same time window, such as under 2 seconds, under 1 second, or under a half a second, for the inputs to be registered as an intentional activation of therapy override. Similarly, the method 300, in other examples not illustrated, may monitor for contemporaneous and/or successive activations of the first and second touch controls repeatedly throughout the predetermined period of time prior to treatment activation in the circumstance where activation of one touch control is not joined or followed by activation of the second touch control.

Additionally, in some examples, certain steps of the method 300 may be performed in a different order or in parallel. For example, activation of the first touch control may be identified prior to registering actuation of the force-activated switch of the second touch control. Other modifications to the method 300 are possible while remaining within the intent and purpose of the method 300.

Figure 3B:
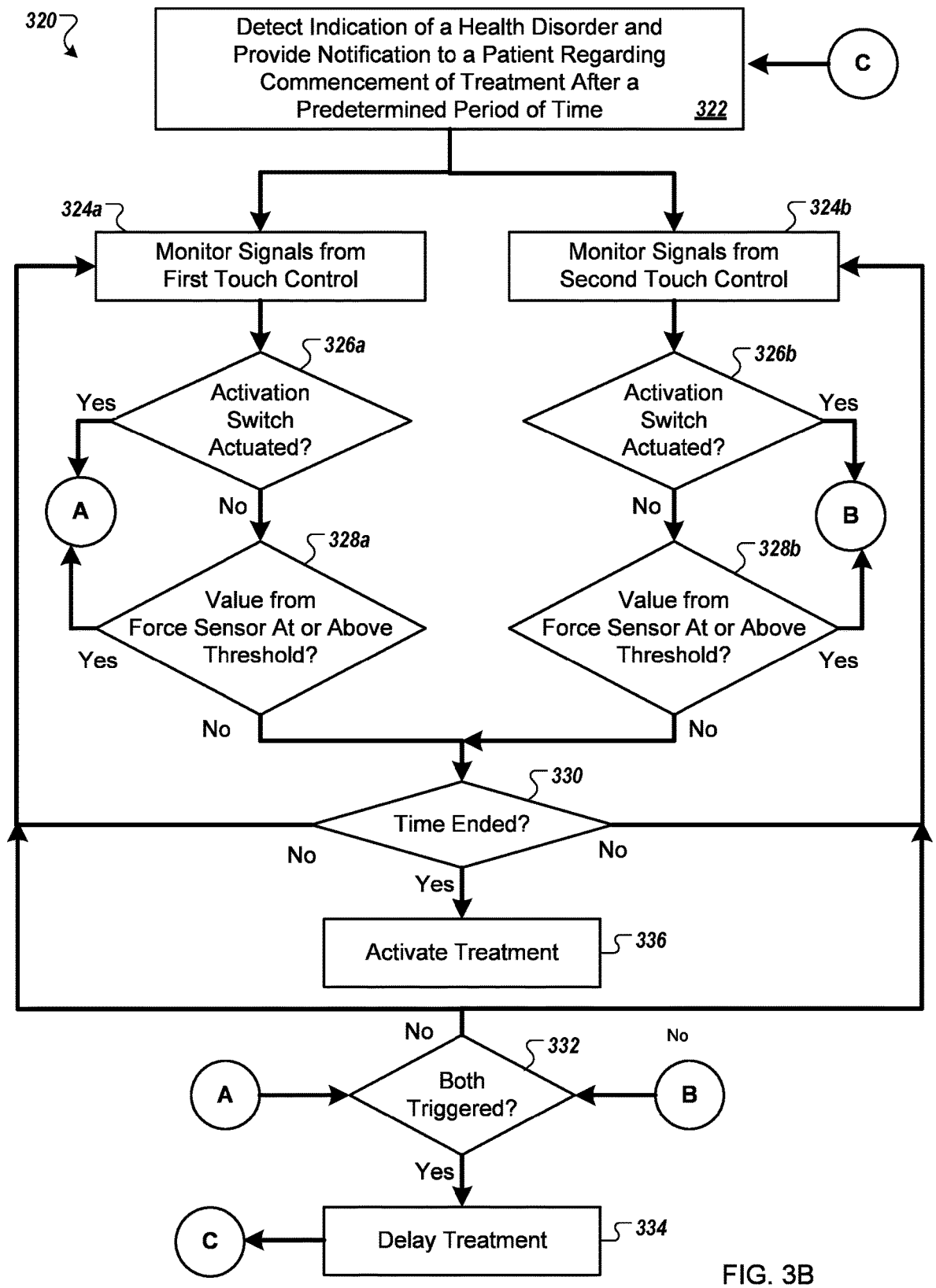
FIG. 3B is a flow chart of an example method for failsafe delay of therapy delivery through signal monitoring of two touch controls each having a force sensor.

FIG. 3B is a flow chart of an example method 320 for failsafe delay of therapy delivery through signal monitoring of two touch controls each having a force sensor. The method 320 includes a number of steps that can be performed by one or more components of a medical device, such as the medical device 600 of FIG. 6, including, in some examples, a computing device or system in communication with the medical device, such as a remote (e.g., cloud-based) computing system or portable computing device. In illustrative examples, the steps of the method 320 may be performed by the control unit 620 of the medical device 600 (or, similarly, control unit 200 of FIG. 2A, control unit 230 of FIG. 2C, or control unit 250 of FIG. 2E), by the control unit of the medical device in combination with a remote computing system, or by a separate computing system or device such as a portable computing device in communication with the medical device.

In some implementations, the method 320 begins with detecting indication of a cardiac anomaly and providing notification to a patient regarding commencement of treatment (322). As discussed in relation to steps 302 and 304 of the method 300, for example, the cardiac anomaly, may be a type of cardiac arrhythmia. The determination may be based on cardiac data such as ECG data.

In some implementations, signals from a first touch control and a second touch control are monitored in parallel (324a, 324b). The signals, in some examples, are monitored in part through shared thresholding circuitry conducting a hardware analysis of outputs of a force sensor of the first touch control and a force sensor of the second touch control. In other examples, the signals are monitored in part through respective threshold circuitry conducting a hardware analysis of outputs of a certain force sensor. The thresholding circuitry, for example, may register that force(s) within a predetermined range of force values have been received.

As illustrated, if either a force-activated switch of the respective touch control is actuated (326a, 326b) or a value at or above a force threshold is registered at a force sensor of the respective touch control (328a,b), in some implementations, the method 320 exits monitoring (324a, 324b) for the touch control. When the respective force-activated switch is actuated (326a,b) or a value of the respective force sensor is at or above a threshold value (326a,b), a trigger event is registered (A, B) and provided to step 332.

Although illustrated as being determined in a certain order, the determinations 326, 328 may be conducted in parallel or in the opposite order, in other examples.

As discussed previously, although described as "a value", in some examples, multiple signals over time may be analyzed to determine the force value at the force sensor, such that a brief errant signal is not misconstrued as a purposeful input by the patient.

In some examples, the threshold value is different between the first touch control and the second touch control. For example, if the patient has a known impairment that effects movement of the thumb differently than movement of the index finger, the touch control situated for actuation by the patient's thumb may be set with a different force threshold than the touch control situated for actuation by the patient's index finger. In one example, a hardware setting may customize a threshold level between a number of predetermined selectable threshold levels. In another example, a software-selectable threshold may be user customizable based test forces applied to the touch controls by the patient during a configuration routine. In a further example, a software-selectable threshold may be customizable in part based upon registered forces during prior user interaction with the first and second touch controls, for example through interacting with a graphical user interface. In a final example, a software-selectable threshold may be determined in part based upon recent patient activity as evidenced through sensor data collected by the control unit. In an example, if the control unit determines via a gyroscope sensor that the patient has recently fallen, the threshold for patient input may be lowered due to the potential for the first touch control and/or the second touch control being in awkward positions for patient activation.

Further, in certain examples, determining whether the value from the force sensor is at or above a threshold force value (328a) additionally includes determining whether the value from the force sensor is below a second threshold force value. For example, determining the value from the force sensor may include determining the force value from the force sensor is less than an actuation force of the force-activated switch mechanism (e.g., within a range from a lower threshold force value up to the actuation force of the force-activated switch).

In some implementations, it is determined whether both the first touch control and the second touch control has been activated (332). In some examples, signals from the first touch control and the second touch control establishing verified activation must overlap (e.g., the signals should be sufficient to register simultaneous or successive activation by the patient with sustained or intermittent (pulsing or varying) force upon both touch controls for some period of time). In other examples, signals from the first touch control and the second touch control establishing verified activation must be received within a certain window of time to be sufficient to register activation by the patient responsive to the notification. The window of time, for example, may be two seconds, one second, or one half of a second. For example, upon registering input from one touch control (trigger event A or trigger event B), the method may begin a timer for receipt of input from the second touch control (trigger event B or trigger event A).

If a trigger even has been detected for only one of the first and second touch controls, in some implementations, the method 320 returns to monitoring signals from the touch controls (324a, 324b). For example, upon falling, a forward-facing touch control may be actuated against an object. Without actuation of the opposite touch control, the control unit assumes the patient is not responsive. However, the control unit may wait the entire predetermined period of time prior to activating treatment (336).

If, instead, trigger events are identified from both the first touch control and the second touch control, in some implementations, treatment is delayed (334). For example, while a defibrillating shock may not be delivered to the patient, the medical device will continue to monitor the sensor data for further evidence of ongoing cardiac anomaly and, upon substantial evidence, may re-initiate the notification (322).

If the predetermined window of time passes without identifying trigger events from both the first touch control and the second touch control, in some implementations, treatment is activated (336). If the patient does not respond, the patient may be presumed to be unconscious. Thus, the treatment sequence may proceed, for example culminating in the delivery of one or more defibrillating shocks to the body of the patient.

Although illustrated in a certain series of steps, in other examples, more or fewer steps may be included in the method 320. For example, as discussed above, the method 320 may additionally monitor a second predetermined window of time such that the trigger events from the first touch control and the second touch control will delay treatment only if both received within the second, shorter, predetermined window of time.

Additionally, in some examples, certain steps of the method 320 may be performed in a different order or in parallel. As discussed above, for example, steps 326 and 328 may be performed in parallel. Other modifications to the method 320 are possible while remaining within the intent and purpose of the method 320.

Figure 3C:
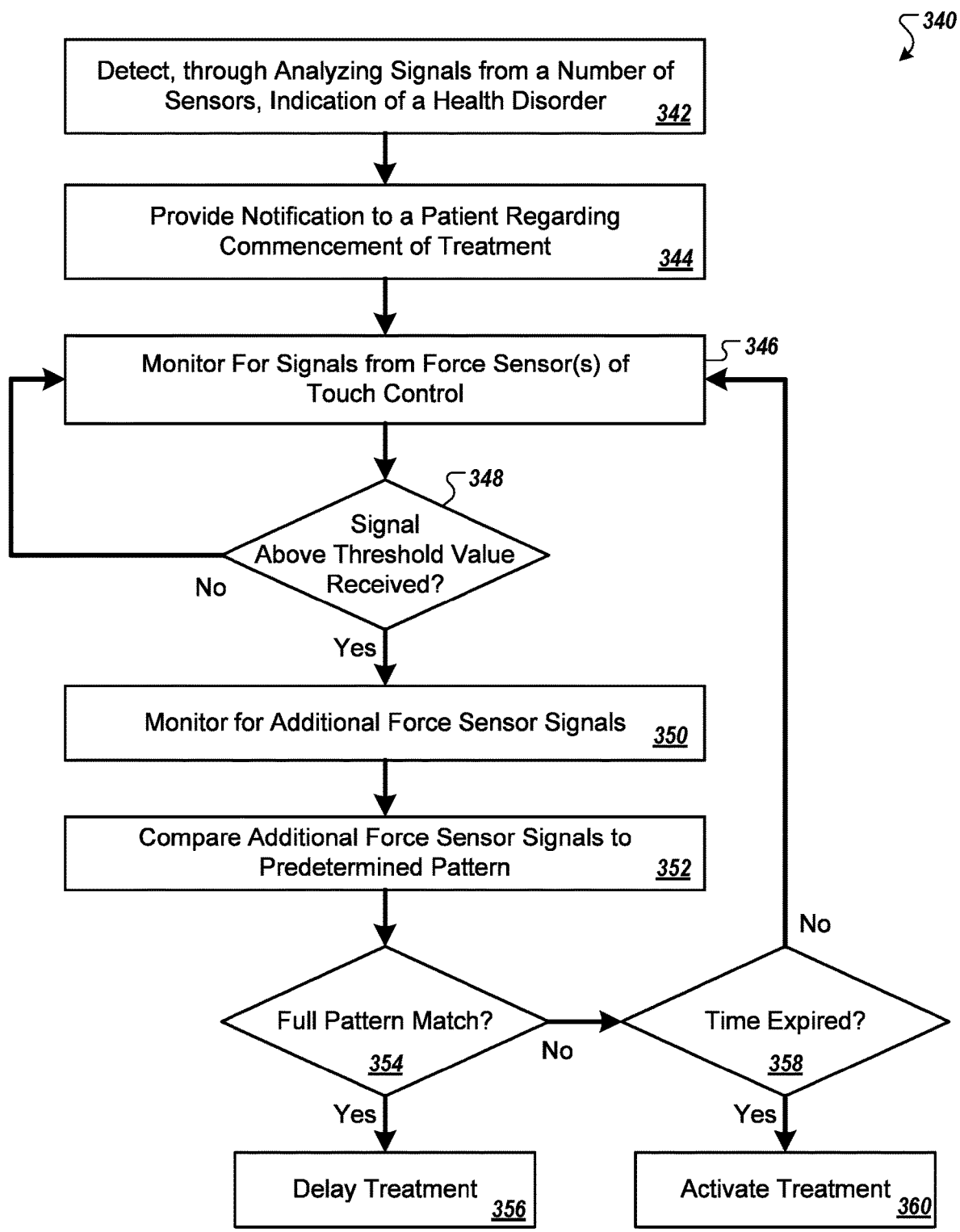
FIG. 3C is a flow chart of an example method for failsafe delay of therapy delivery through signal monitoring of a single touch control having a force sensor.

FIG. 3C is a flow chart of an example method 340 for failsafe delay of therapy delivery through signal monitoring of a single touch control having a force sensor. The method 340 includes a number of steps that can be performed by one or more components of a medical device, such as the medical device 600 of FIG. 6, including, in some examples, a computing device or system in communication with the medical device, such as a remote (e.g., cloud-based) computing system or portable computing device. In illustrative examples, the steps of the method 340 may be performed by the control unit 620 of the medical device 600 (or, similarly, control unit 200 of FIG. 2A, control unit 230 of FIG. 2C, or control unit 250 of FIG. 2E), by the control unit of the medical device in combination with a remote computing system, or by a separate computing system or device such as a portable computing device in communication with the medical device.

In some implementations, the method 340 begins with detecting indication of a cardiac anomaly through analyzing signals from a number of sensors (342). As discussed in relation to step 302 of the method 300 of FIG. 3A, for example, the cardiac anomaly, may be a type of cardiac arrhythmia. The determination may be based on cardiac data such as ECG data.

In some implementations, a notification is provided to a patient regarding commencement of treatment (344). As discussed in relation to step 306 of the method 300 of FIG. 3A, for example, the patient may be alerted regarding commencement of treatment via a verbal message or shrill alarm. The patient may also be instructed to activate a touch control on the control unit or on the user interface pod of the medical device to indicate that the patient is conscious, thereby instructing the control unit or medical device to withhold the delivery of one or more therapeutic defibrillating shocks.

The instructions in the notification, in some examples, include instructions for inputting one or more touches indicative of patient interaction as opposed to accidental actuation of the touch control due to an object pressing against the touch control. In a first example, the patient may be instructed to perform a single touch entry through slowly pressing then slowly releasing the touch control. In a second example, the patient may be instructed to perform a series of touch interactions.

In some implementations, signals from one or more force sensors of a touch control are monitored for patient response to the notification (346). The signals, for example, may include signals from at least one force sensor such as the force sensors 104a,b of FIG. 1A. Further, in some examples, the signals may include signals from multiple force sensors disposed in series and/or in parallel as discussed, for example, in relation to FIGS. 1B-1D.

In some implementations, if one or more signals above a threshold value are received from the force sensor(s) (348), additional force sensor signals are monitored (350). For example, the initial one or more signals may constitute a first input from the patient, while future one or more signals may be indicative of a subsequent input by the patient. Each touch interaction by the patient, for example, would be separated by a period of time of low to no signal traffic from the force sensor(s), indicative of the patient having released the touch control.

In some implementations, the additional force sensor signals are compared to a predetermined pattern (352). The predetermined pattern, in some examples, includes slow application and removal of force to the force sensor. In this example, the predetermined pattern may be a ramping and releasing of force indicative of a "slow press" entered by the patient. In this example, the "predetermined pattern" includes only one input from the patient. In further examples, two or more distinct patient inputs may be analyzed to ensure purposeful patient inputs to the touch control. For each touch control event, for example, the ramping and release of force upon the force sensor indicative of a patient pressing upon the touch control may be used to indicate a purposeful entry by the patient. In another example, each touch control event may involve multiple pulses of force (e.g., forces registered at variable intervals) input by the patient. For example, where the patient has a tremor or other inability to assert a consistent force against the force control, the touch events may each be recognized as periods of pulsed forces indicative of the patient pressing upon the touch control.

The predetermined pattern, in some examples, includes inputting a pattern responsive to receiving the pattern from the medical device in real time. For example, the instructions may include instructions for performing a series of touch interactions, each interaction being separately prompted by the control unit or medical device. For example, a noise, display, and/or haptic vibration may cue the patient to enter each new touch interaction.

In some implementations, the predetermined pattern is customized based upon patient training and/or patient capability. For example, during setup with a medical professional, an appropriate pattern response may be selected from a collection of possible pattern responses to ensure patient ability to enter the pattern during a stressful event (e.g., shrill alarms warning of imminent electrical therapy). In another example, the pattern response may be selected in part based upon present conditions as determined through analysis of one or more additional sensors. For example, signals from an accelerometer, a gyroscope, or a magnetometer may be indicative of a present condition of the patient such as, in some examples, riding in a moving vehicle, recently fallen, or in a restful state.

If a full pattern match is identified (354), in some implementations, treatment is delayed (356). For example, while a defibrillating shock may not be delivered to the patient, the medical device will continue to monitor the sensor data for further evidence of ongoing cardiac anomaly and, upon substantial evidence, may re-initiate the notification (344).

If, instead, the full pattern match is not identified (354), the method 340, in some implementations, attempt to reinitiate the pattern matching with the patient prior to expiration of the predetermined period of time (358).

If the full pattern match is not identified (354) and the predetermined period of time has expired, in some implementations, treatment is activated (360). If the patient does not respond, the patient may be presumed to be unconscious. Thus, the treatment sequence may proceed, for example culminating in the delivery of one or more defibrillating shocks to the body of the patient.

Although illustrated in a particular series of steps, in other examples, more or fewer steps may be included in the method 340. For example, a first notification may be provided to request user response (344), while subsequent notification(s) (not illustrated) may request confirmation of user response through repetition of user entry. Further, in some examples, the notification (344) may provide instructions for following a visual, haptic, and/or audible cue for patient entry of touch responses to the touch control, followed by such cues (not illustrated). Further, in some examples, rather than monitoring for additional force sensor signals (350), a single touch input, such as a slow application of force followed by a slow removal of force, may be determined adequate for comparison and identification of the predetermined pattern (352, 354).

Additionally, in some examples, certain steps of the method 340 may be performed in a different order or in parallel. For example, each step of the predetermined pattern may be validated through analysis, in other examples, rather than comparing additional sensor signals to the predetermined pattern (352) after monitoring (350). Other modifications to the method 340 are possible while remaining within the intent and purpose of the method 340.

Figure 5:
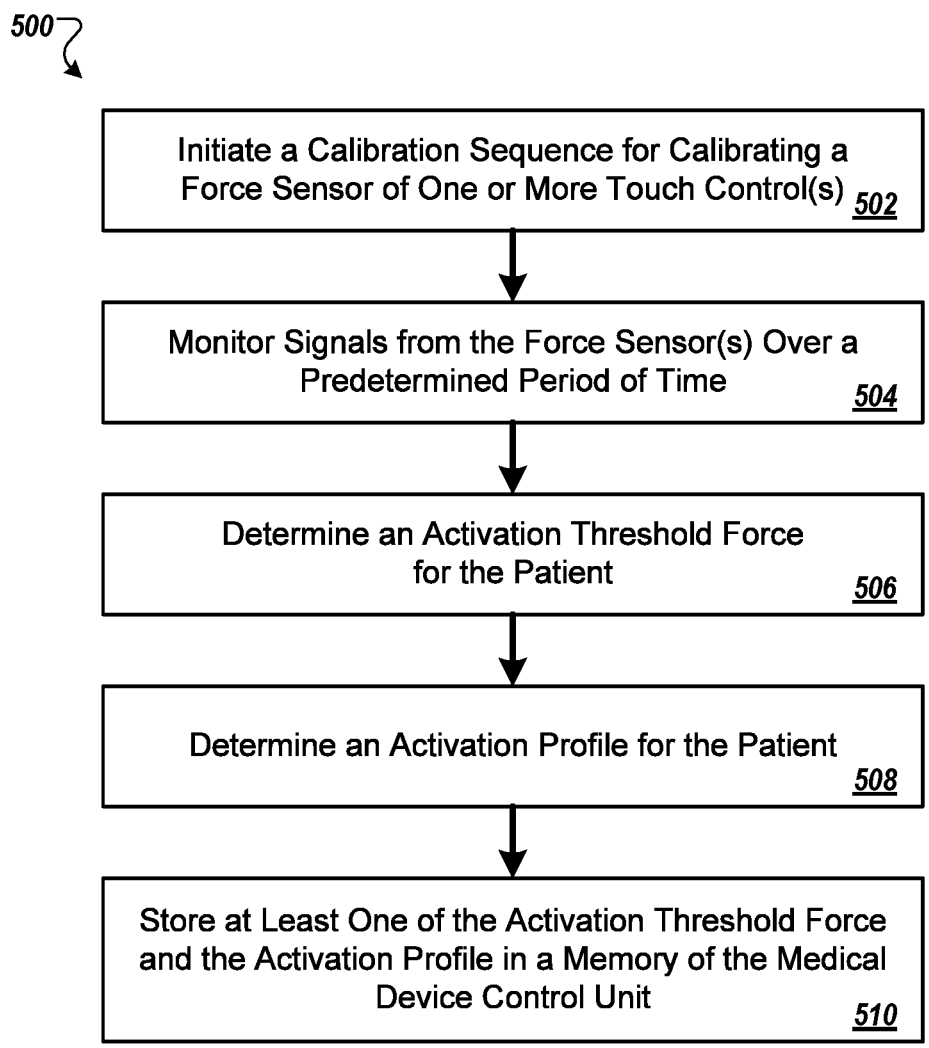
FIG. 5 is a flow chart of an example method for calibrating a touch control having a force sensor.

In some examples, the control unit is configured to calibrate analysis of signals from the force sensor based upon the patient's ability to apply force to the touch control. FIG. 5 is a flow chart of an example method 500 for calibrating a touch control having a force sensor. The method 500 includes a number of steps that can be performed by one or more components of a medical device, such as the medical device 600 of FIG. 6, including, in some examples, a computing device or system in communication with the medical device, such as a remote (e.g., cloud-based) computing system or portable computing device. In illustrative examples, the steps of the method 500 may be performed by the control unit 620 of the medical device 600 (or, similarly, control unit 200 of FIG. 2A, control unit 230 of FIG. 2C, or control unit 250 of FIG. 2E), by the control unit of the medical device in combination with a remote computing system, or by a separate computing system or device such as a portable computing device in communication with the medical device.

In some implementations, the method 500 begins with initiating a calibration sequence for calibrating a force sensor of one or more touch controls (502). The calibration sequence is initiated during a visit with a medical professional through entering a calibration phrase of the setup of the control unit. For instance, the calibration may be performed during an initial baselining phase prior to or during initial deployment of the device to the patient. In certain examples, the calibration sequence runs as a background task while the patient uses the touch control(s) for common tasks, such as while interface with a graphical user interface of the control unit. In further examples, the calibration sequence may execute periodically, prompting the patient outside of medical professional visits to interact with the touch control(s) for calibration purposes.

In some implementations, signals are monitored from the force sensor over a predetermined period of time (504). The period of time, in some examples, may be at least a half second, at least a second, or at least two seconds. The period of time, in some examples, is selected based in part upon a visual, audible, and/or haptic notification provided to the user. In some examples, the user may be instructed to quickly press and release the touch control (e.g., press and release between 2-5 number of times within a second), slowly press and release the touch control (e.g., pressure and release between 2-5 times within 3 seconds), press and hold the touch control while a lamp is lit upon the control unit or while a graphic is visible on a screen of the control unit, or press and hold the touch control until receiving a haptic feedback (e.g., vibration) signaling release. In other examples, the period of time is selected based in part upon a current interaction between the user and the control unit. For example, where the user is attempting to activate the graphical user interface, the user may need to pinch and release two touch controls disposed upon opposite surfaces of the control unit.

In some examples, the signals represent a single press action by the patient. For example, the patient may be expected to enter a single touch interaction (e.g., in waking up the graphical user interface) or prompted to enter a single touch interaction. In other examples, the signals represent multiple touch interactions. For example, the user may be prompted to press and release the touch control X times (e.g., twice, three times, five times) to calibrate an average force applied upon activating the touch control.

In some examples, monitoring may cease prior to the end of the predetermined period of time based upon a cessation of force by the patient. For example, where the user is expected to enter a single touch interact, and a touch interaction followed by negligible force application to the force sensor, the monitoring may cease.

In some implementations, an activation threshold force is determined for the patient using the signals provided to the force sensor within the predetermined period of time (506). The activation threshold force, for example, may represent a minimum force setting for the control unit to register actuation (e.g., a lower boundary of a range of forces indicative of intentional actuation). For example, a mean, median, or average force upon the force sensor may be determined in establishing an activation threshold force for the force sensor(s). In some examples, the activation threshold force is the same for all touch controls. In other examples, separate threshold forces may be determined for each touch control. The activation threshold, in some examples, is customized to the user (e.g., directly indicative of capability of the patient to apply force to the touch control(s)). In other examples, the activation threshold is selected from a limited number of activation thresholds based upon the patient's ability to apply force to the touch control(s). For example, the force sensor output may be analyzed in part through a hardware-based thresholding, and the software may be configured to select between one of N (e.g., two, three, four, five, etc.) possible thresholds wired into the hardware-based thresholding circuitry.

In some implementations, an activation profile is determined for the patient (508), for example, during an initial baselining phase. The activation profile, for example, may capture the patient's ability to interact with the touch controls(s) as both typical (average, mean, or median) forces applied to the touch control(s) as well as, in some examples, maximum forces applied to the touch control(s). The patient, in some examples, may be determined to be incapable of actuating a force-activated switch of the touch control(s) at least part of the time. In these circumstances, the activation profile may aid in establishing criteria for interpreting signals from the force sensor of each of the touch control(s) to identify purposeful inputs supplied by the patient.

The activation profile, in some examples, includes nuances of force applied by the patient over time. The nuances, in an illustrative example, may include a pulsed application of force (e.g., forces registered at variable intervals) due to a physiological disorder leading to a tremor or tic. Further, the nuances may include, in some examples, sustained ability over time to apply force(s) to the touch control(s), patient interpretation of the instruction of "long" press or "short" press upon the touch control(s), and/or patient ability to correctly enter patterns via activating the touch control(s) responsive to prompts.

In some implementations, at least one of the activation threshold force and the activation profile is stored in a memory of the medical device control unit (510). The activation threshold force and/or activation profile, for example, may be used in analyzing signals obtained through the touch control(s) in identifying purposeful activations of the touch control(s) by the patient. In some examples, the activation threshold force and/or activation profile may be applied at step 312 of method 300 of FIG. 3A, steps 328*a,b* of method 320 of FIG. 3B, or step 348 of method 340 of FIG. 3C. In other examples, the activation threshold force may be used to select one of a set of predetermined threshold values without storing the information for long term use.

Although illustrated in a certain series of steps, in other examples, more or fewer steps may be included in the method 500. For example, in some examples, historic activation threshold force(s) or activation profile(s) may be used to adjust these values over time as the patient's strength or disorder symptoms vary.

Additionally, in some examples, certain steps of the method 500 may be performed in a different order or in parallel. For example, the activation profile may be determined (508) in parallel or before determining the activation threshold force (506). Other modifications to the method 500 are possible while remaining within the intent and purpose of the method 500.

The teachings of the present disclosure can be generally applied to external medical monitoring and/or treatment devices (e.g., devices that are not completely implanted within the patient's body). External medical devices can include ambulatory medical devices that are, for example, capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, heart vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung vibrations (e.g., using microphones and/or accelerometers positioned over the patient's thoracic area), breath vibrations, sleep related parameters (e.g., snoring, sleep apnea), tissue fluids (e.g., using radio-frequency transmitters and sensors), among others. For example, a vibrational analysis of vibrations detected via a thoracic vibrations sensor can provide information about characteristic vibrational patterns. The vibrational analysis includes monitoring for vibrations ranging from $\frac{1}{10}$th to about 1 Hz for monitoring low frequency thoracic cavity movements such as breathing, chest wall movements, and, in some cases, heart wall movements. For example, where the sensor is substantially aligned with an apex of a ventricle of the patient, the sensor implementing vibrational analysis can detect and monitor ventricular wall motion. Similarly, other vibrational patterns can be monitored. Certain lung vibrations have characteristic patterns at various frequencies including at around 100-5000 Hz (e.g., tracheal vibrations), >500 Hz (e.g., stridor), >100-5000 Hz (e.g., wheezing), –150 Hz (e.g., rhonchus), and <350 Hz (e.g., pleural friction). Frequencies involving heart vibrations and murmurs are typically in a range from around 20 to 500 Hz. Low frequency heart vibrations are those where the dominant frequencies are less than around 100 Hz, such as S3, S4, and diastolic murmur of mitral stenosis. Certain murmurs have higher frequency components such as aortic regurgitation, where dominant frequencies are around 400 Hz.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a number of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In some implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, an example of a therapeutic medical device can include a short-term continuous monitoring and/or neuromodulator for autonomic cardiovascular control, for example, a short-term outpatient wearable Tragus nerve stimulator. In such an example implementation of the short-term wearable neuromodulator, the electrode assembly can be attached to the patient's Tragus of their ear. One or more electrodes can be positioned to and configured to activate afferent branch of the patient's Vagus nerve and, potentially, other sensory nerves in that region.

In some implementations, the medical device may be a patient monitoring device. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, heart vibrations (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart vibrations (e.g., using accelerometers or microphones), lung vibrations, breath vibrations, sleep related parameters (e.g., snoring, sleep apnea), tissue fluids, among others.

In certain implementations, the medical device is configured to receive additional sensor/patient data from a remote computing device. In an example, patient specific data may be available on a local computing device in communication with the medical device, such as a portable computing device or recharging/communication system designed to operate with the medical device. In another example, the patient specific data may be supplied from a remote computing device, such as a cloud-based server system directly or indirectly in communication with the medical device. For example, the medical device may be placed in communication with the cloud-based server system via another local computing device such as a portable smart device or a recharging/communication system. Further, one or more additional sensor(s) external to wearable medical device (e.g., integrated in another portable health monitoring system carried or worn by the patient, etc.) may supply at least a portion of the patient specific data. The patient specific data, for example, may be provided to the medical device from the additional sensor(s) directly via a wireless communications system, or indirectly through interfacing with an intermediate system such as a portable computing device or recharging/communication system. In some examples, the patient specific data can include age, BMI, known diseases or disorders, and/or current medications. The patient specific data, in further examples, can include baseline data such as resting heart rate or resting respiration.

Figure 6:
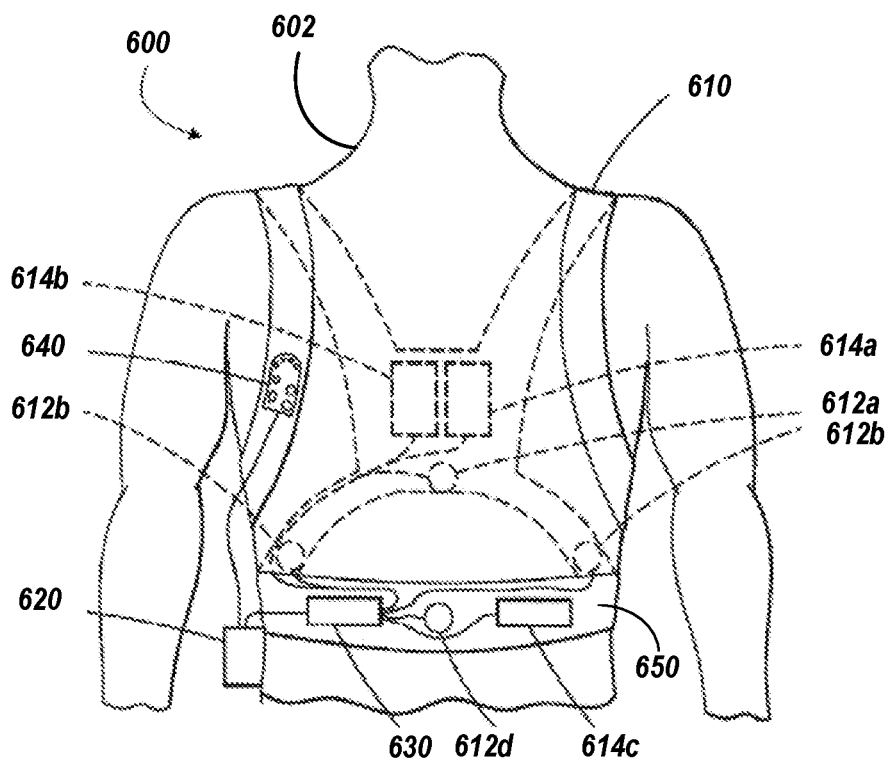
FIG. 6 depicts an example wearable medical device including a defibrillator vest.

FIG. 6 illustrates an example medical device 600 that is external, ambulatory, and wearable by a patient 602, and configured to implement one or more processes described herein. For example, the medical device 600 can be a non-invasive medical device configured to be located substantially external to the patient. Such a medical device 600 can be, for example, an ambulatory medical device that is capable of and designed for moving with the patient as the patient goes about his or her daily routine. For example, the medical device 600 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 600 can include one or more of the following: a garment 610, multiple sensing electrodes 612a-c (e.g., ECG electrodes, collectively referred to herein as sensing electrodes 612), one or more therapy electrodes 614a-c (collectively referred to herein as therapy electrodes 614), a medical device control unit 620, a connection pod 630, a patient interface pod 640, a belt 650, ECG circuitry, or any combination of these. In some examples, at least some of the components of the medical device 600 can be configured to be removably affixed to the garment 610 (or in some examples, permanently integrated into the garment 610 in a manner designed such that the patient is unable to separate the component(s) from the garment 610), which can be worn about the patient's torso. In an example, the one or more touch electrodes can be coupled to the garment using snaps (not shown).

The medical device control unit 620 can include a memory in communication with the ECG circuitry and at least one processor in communication with the memory and the ECG circuitry. The medical device control unit 620 can be operatively coupled to the sensing electrodes 612 and the one or more touch electrodes 660a-e via the ECG circuitry. The connection pod 630 can, in some examples, include a signal processor configured to amplify, filter, and digitize these cardiac signals prior to transmitting the cardiac signals to the ECG circuitry of the medical device control unit 620.

In some examples, the sensing electrodes 612 are affixed to the garment 610. For example, one or more of the sensing electrodes 612 may be assembled into the garment 610 or removably attached to the garment, such as by using hook and loop fasteners. In some implementations, the sensing electrodes 612 are permanently integrated into the garment 610 (e.g., designed to be not removed by the patient wearing the garment).

Component configurations other than those shown in FIG. 6 are possible. For example, the sensing electrodes 612 can be configured to be attached at various positions about the body of the patient 602. The sensing electrodes 612 can be operatively coupled to the medical device control unit 620 through the connection pod 630. In some implementations, the sensing electrodes 612 can be adhesively attached to the patient 602. In some implementations, the sensing electrodes 612 and at least one of the therapy electrodes 614 can be included on a single integrated patch and adhesively applied to the patient's body.

The sensing electrodes 612 can be configured to detect one or more cardiac signals. Examples of such signals include ECG signals and/or other sensed cardiac physiological signals from the patient. Example sensing electrodes 612 include conductive electrodes (e.g., silver/silver chloride electrodes, as described further below) or dry electrodes (e.g., a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference).

In certain implementations, the sensing electrodes 612 can be incorporated into sensing devices including additional components such as accelerometers, acoustic signal detecting components, and other measuring components for recording additional parameters. For example, the sensing electrodes 612 can be incorporated into sensing devices also configured to detect other types of patient physiological parameters and acoustic signals, such as tissue fluid levels, heart vibrations, lung vibrations, respiration vibrations, patient movement, etc.

One or more of the therapy electrodes 614, in some implementations, are configured to deliver one or more therapeutic defibrillating shocks to the body of the patient 602 when the medical device 600 determines that such treatment is warranted based on the signals detected by the sensing electrodes 612 and processed by the medical device control unit 620. Example therapy electrodes 614 can include conductive metal electrodes such as stainless-steel electrodes that include, in certain implementations, one or more conductive gel deployment devices configured to deliver conductive gel to the metal electrode prior to delivery of a therapeutic shock. In some examples, the therapy electrodes 614 are incorporated into sensing devices including one or more additional sensors configured to detect ECG signals as well as other physiological signals of the patient.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 614 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or for a specific patient.

Figure 7:
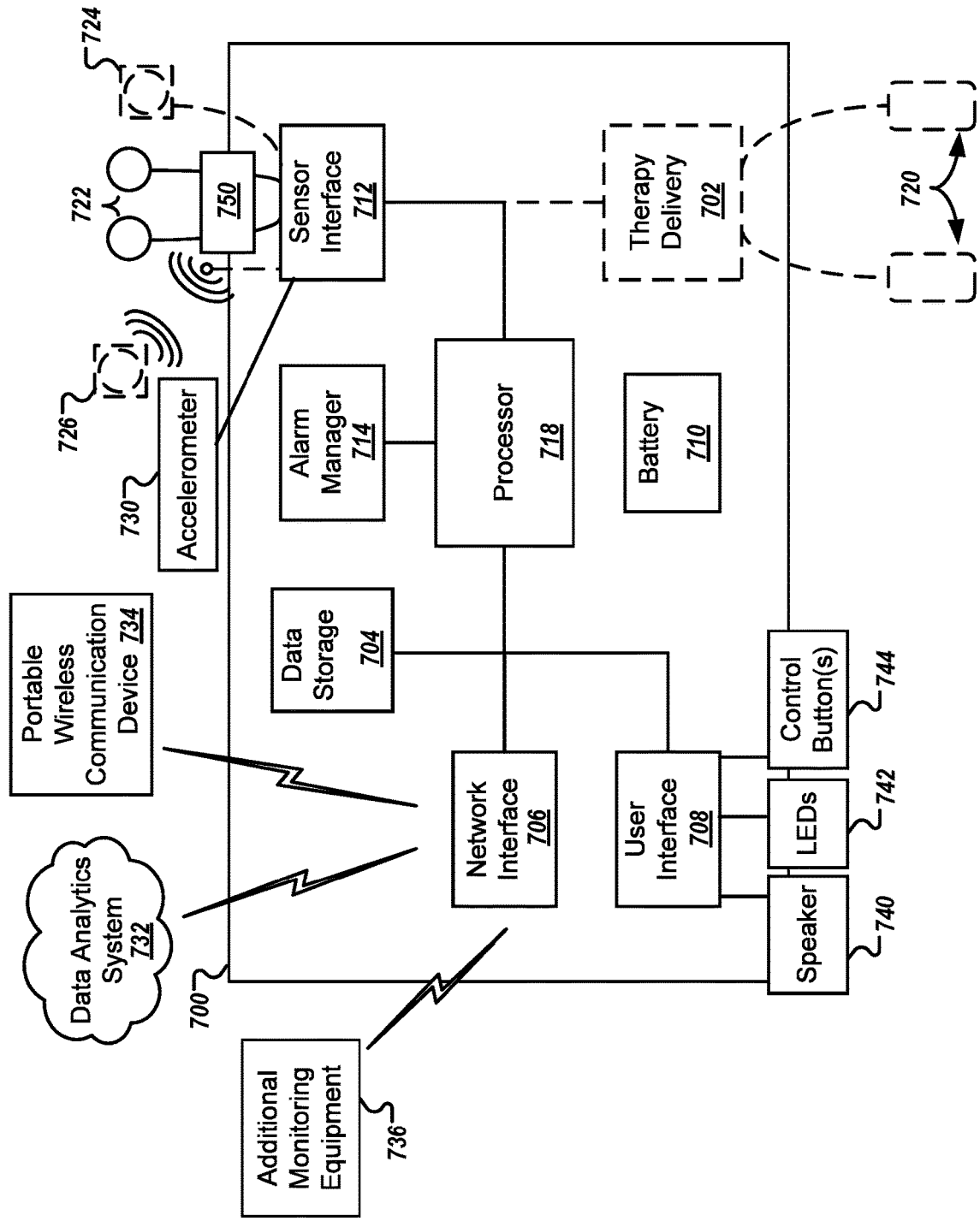
FIG. 7 is a block diagram of an example system for obtaining health metrics and delivering a therapy to a patient using a wearable medical device with a control unit and one or more touch controls with force sensors.

FIG. 7 illustrates a sample component-level view of a medical device controller, such as the medical device control unit 200 of FIGS. 2A-B, control unit 230 of FIGS. 2C-D, control unit 250 of FIG. 2E, or control unit 620 of FIG. 6. As shown in FIG. 7, the medical device controller 700 can include a therapy delivery circuit 702, a data storage 704, a network interface 706, a user interface 708, at least one battery 710, a sensor interface 712, an alarm manager 714, and at least one processor 718. Further, a patient monitoring medical device, such as the medical device 600 of FIG. 6, can include the medical device controller 700. Most or all of the components of the medical device controller 700 may be confined in a same housing of a control unit for a medical device 600, such as the control unit 200 of FIGS. 2A-B, control unit 230 of FIGS. 2C-D, control unit 250 of FIG. 2E, or control unit 620 of FIG. 6.

The therapy delivery circuit 702 can be coupled to one or more electrodes 720 configured to provide therapy to the patient (e.g., therapy electrodes 514 as described above in connection with FIG. 5). For example, the therapy delivery circuit 702 can include, or be operably connected to, circuitry components that are configured to generate and provide the therapeutic shock. The circuitry components can include, for example, resistors, capacitors, relays and/or switches, electrical bridges such as an h-bridge (e.g., including multiple insulated gate bipolar transistors or IGBTs), voltage and/or current measuring components, and other similar circuitry components arranged and connected such that the circuitry components work in concert with the therapy delivery circuit and under control of the at least one processor (e.g., processor 718) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank having multiple capacitors (e.g., two, three, four or more capacitors). These capacitors can be switched into a series connection during discharge for a defibrillation pulse. For example, four capacitors of approximately 650 uF can be used. The capacitors can have between 350 to 500-volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 702 can be configured to perform the switching and pulse delivery operations, e.g., under control of the at least one processor 718. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 704 can include one or more of non-transitory computer readable media, such as flash memory, solid state memory, magnetic memory, optical memory, cache memory, combinations thereof, and others. The data storage 704 can be configured to store executable instructions and data used for operation of the medical device controller 700. In certain implementations, the data storage can include executable instructions that, when executed, are configured to cause the at least one processor 718 to perform one or more functions, such as portions of the methods described in relation to FIGS. 3A, 3B, and 3C or the method described in relation to FIG. 5.

In some examples, the network interface 706 can facilitate the communication of information between the medical device controller 700 and one or more other devices or entities over a communications network. For example, the network interface 706 can be configured to communicate with a remote data analytics system 732 such as a remote server, cloud computing environment, or other similar computing device. The remote data analytics system 732, for example, may be used to perform analysis and historic comparison of data derived through the sensor interface 712.

The network interface 706, in some implementations, can facilitate communication between the medical device controller 700 and a portable wireless communication device 734. In some examples, rather than directly communicating with the data analytics system 732, the portable wireless communication device 734 may provide a network conduit, for example receiving data from the medical device controller 700 via a short-range communication link such as a Bluetooth or RF communication interface provided by the network interface 706. The portable wireless communication device 734 may then perform some local analysis of the data and/or communicate the data to the data analytics system 732. Further, in some examples, the portable wireless communication device 734 may provide user interface capabilities beyond the capabilities of the user interface 708. For example, while the medical device may be directly attached to the patient and therefore not readily observed for receiving information such as text messages or lighted displays, an enhanced patient interface may be presented to the patient through coordinating communications with the portable wireless communication device 734.

In some implementations, the network interface 706 is configured to communicate with additional monitoring equipment 736, such as, in some examples, a pulse monitoring device, sleep apnea monitoring device, respiratory monitoring device, or other biometric collection device. This additional patient data may be used by the processor and/or the data analytics system 732 to fine-tune analysis.

In certain implementations, the user interface 708 can include one or more physical interface devices such as input devices, output devices, and combination input/output devices and a software stack configured to drive operation of the devices. These user interface elements may render visual, audio, and/or tactile content. Thus, the user interface 708 may receive input or provide output, thereby enabling a user to interact with the medical device controller 700. In examples, the user interface 708 may include a speaker element 740 and light emitting diodes (LEDs) 742. Further, in some implementations, the user interface 708 includes one or more control buttons 744 for providing settings communication and/or for supplying a response upon the alarm manager 714 triggering an alert regarding an unresponsive patient. The control buttons 744, for example, may override functionality by indicating that the patient is not unconscious. At least one of the control buttons 744 may include a force sensor such as the force sensors 104a,b described in relation to FIG. 1A, the force sensor 120 of FIG. 1B, the force sensor 130 of FIG. 1C, or the force sensor 140 of FIG. 1D.

The medical device controller 700 can also include at least one battery 710 configured to provide power to one or more components integrated in the medical device controller 700. The battery 710 can include a rechargeable multi-cell battery pack. In one example implementation, the battery 710 can include three or more 2200 mAh lithium ion cells that provide electrical power to the other device components within the medical device controller 700. For example, the battery 710 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 700.

The sensor interface 712 can be coupled to one or more sensors configured to monitor one or more physiological parameters of the patient. As shown, the sensors may be coupled to the medical device controller 700 via a wired or wireless connection. The sensors can include one or more electrocardiogram (ECG) electrodes 722, heart vibrations sensors 724, and tissue fluid monitors 726 (e.g., based on ultra-wide band radiofrequency devices).

The ECG electrodes 722 can monitor a patient's ECG information. For example, the ECG electrodes 722 can be conductive electrodes, e.g., a metallic element disposed on a substrate and in some cases, includes an electrolytic gel to facilitate ECG detection. As an example, such conductive ECG electrodes are composed of a plastic substrate covered with a silver/silver chloride ionic compound. Silver chloride is only very slightly soluble in water, so it can remain relatively stable. The conductive electrode can be assembled with an electrolyte gel in which a principle anion is Cl−. Cl− is an attractive anion for electrode applications because the skin interface contains an excess of chloride ions in solution (e.g., perspiration).

In some implementations, the ECG electrodes 722 can be dry electrodes, e.g., a metallic element substrate with an oxide coating disposed on a substrate. Dry electrodes comprise metal electrodes with oxide coatings such as tantalum pentoxide electrodes, as described in, for example, U.S. Pat. No. 6,253,099 entitled "Cardiac Monitoring Electrode Apparatus and Method," the content of which is incorporated herein by reference.

The ECG electrodes 722 are configured to measure changes in a patient's electrophysiology by measuring the patient's ECG information. ECG circuitry 750 associated with the ECG electrodes 722 can transmit information descriptive of the ECG signals to the sensor interface 712 for subsequent analysis.

The heart vibrations sensors 724 can detect a patient's heart vibration information. For example, the heart vibrations sensors 724 can be configured to detect heart vibration values including any one or all of S1, S2, S3, and S4. From these heart vibration values, certain heart vibration metrics may be calculated, including any one or more of EMAT, % EMAT, SDI, and LVST. The heart vibrations sensors 724 can include an acoustic sensor configured to detect vibrations from a subject's cardiac system and provide an output signal responsive to the detected heart vibrations. The heart vibrations sensors 724 can also include a multi-channel accelerometer 730, for example, a three channel accelerometer configured to sense movement in each of three orthogonal axes such that patient movement/body position can be detected and correlated to detected heart vibrations information. The heart vibrations sensors 724 can transmit information descriptive of the heart vibrations information to the sensor interface 712 for subsequent analysis.

The tissue fluid monitors 726 can use RF based techniques to assess fluid levels and accumulation in a patient's body tissue. For example, the tissue fluid monitors 726 can be configured to measure fluid content in the lungs, typically for diagnosis and follow-up of pulmonary edema or lung congestion in heart failure patients. The tissue fluid monitors 726 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 726 can transmit information descriptive of the tissue fluid levels to the sensor interface 712 for subsequent analysis.

The sensor interface 712 can be coupled to any one or combination of sensing electrodes/other sensors to receive other patient data indicative of patient parameters via the ECG circuitry 750. Once data from the sensors has been received by the sensor interface 712, the data can be directed by the at least one processor 718 to an appropriate component within the medical device controller 700. For example, if heart data is collected by heart vibrations sensor 724 and transmitted to the sensor interface 712, the sensor interface 712 can transmit the data to the at least one processor 718 which, in turn, relays the data to a cardiac event detector. The cardiac event data can also be stored on the data storage 704.

In certain implementations, the alarm manager 714 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 714 can be implemented using hardware or a combination of hardware and software. For instance, in some examples, the alarm manager 714 can be implemented as a software component that is stored within the data storage 704 and executed by the at least one processor 718. In this example, the instructions included in the alarm manager 714 can cause the at least one processor 718 to configure alarm profiles and notify intended recipients using the alarm profiles. In other examples, alarm manager 714 can be an application-specific integrated circuit (ASIC) that is coupled to the at least one processor 718 and configured to manage alarm profiles and notify intended recipients using alarms specified within the alarm profiles. Thus, examples of alarm manager 714 are not limited to certain hardware or software implementation.

In some implementations, the at least one processor 718 includes one or more processors (or one or more processor cores) that each are configured to perform a series of instructions that result in manipulated data and/or control the operation of the other components of the medical device controller 700. In some implementations, when executing a specific process (e.g., cardiac monitoring), the at least one processor 718 can be configured to make specific logic-based determinations based on input data received, and be further configured to provide one or more outputs that can be used to control or otherwise inform subsequent processing to be carried out by the at least one processor 718 and/or other processors or circuitry with which processor 718 is communicatively coupled. Thus, the at least one processor 718 reacts to specific input stimulus in a specific way and generates a corresponding output based on that input stimulus. In some example cases, the at least one processor 718 can proceed through a sequence of logical transitions in which various internal register states and/or other bit cell states internal or external to the at least one processor 718 may be set to logic high or logic low. As referred to herein, the at least one processor 718 can be configured to execute a function where software is stored in a data store coupled to the at least one processor 718, the software being configured to cause the at least one processor 718 to proceed through a sequence of various logic decisions that result in the function being executed. The various components that are described herein as being executable by the at least one processor 718 can be implemented in various forms of specialized hardware, software, or a combination thereof. For example, the at least one processor can be a digital signal processor (DSP) such as a 24-bit DSP processor. The at least one processor can be a multi-core processor, e.g., having two or more processing cores. The at least one processor can be an Advanced RISC Machine (ARM) processor such as a 32-bit ARM processor. The at least one processor can execute an embedded operating system, and include services provided by the operating system that can be used for file system manipulation, display & audio generation, basic networking, firewalling, data encryption and communications.

Although the subject matter contained herein has been described in detail for the purpose of illustration, it is to be understood that such detail is solely for that purpose and that the present disclosure is not limited to the disclosed examples, but, on the contrary, is intended to cover modifications and equivalent arrangements that are within the spirit and scope of the appended claims. For example, it is to be understood that the present disclosure contemplates that, to the extent possible, one or more features of any example can be combined with one or more features of any other example.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable medical device having a customizable force-sensitive patient control interface, the wearable medical device comprising:
one or more cardiac sensing electrodes configured to monitor one or more cardiac physiological parameters of a patient;
a therapy delivery circuit configured to deliver therapeutic pulses to a heart of the patient; and
a controller configured to
receive signals from the one or more cardiac sensing electrodes, and
determine, using the signals, whether to cause delivery of the therapeutic pulses via the therapy delivery circuit,
the controller comprising
one or more response buttons, wherein
at least one response button of the one or more response buttons comprises a force-sensitive sensor configured to register a force corresponding to the patient pressing on the at least one response button,
a memory configured to store a minimum force value representing a threshold level for registering purposeful activation of the at least one response button, and
processing circuitry in communication with the memory;
wherein the processing circuitry of the controller is configured to
customize, via a settings function of the controller, the minimum force value, wherein
the minimum force value is below an actuation force of the at least one response button, and
the minimum force value is selectable between at least two possible values for the threshold level, and
after customizing the minimum force value, monitor, over a predetermined period of time, for an input from the patient at the at least one response button based on signals from the force-sensitive sensor of each response button of the at least one response button, wherein the monitoring comprises
analyzing a first signal from the force-sensitive sensor of a given response button of the at least one response button to identify application of a wearer force below the actuation force,
determining that a force value of the wearer force is in a range from the minimum force value to the actuation force, and
responsive at least in part to detecting application of the wearer force in the range, registering the input.

2. The wearable medical device of claim 1, wherein the at least two possible values for the threshold level are at or greater than 80 g-f.

3. The wearable medical device of claim 1, wherein the actuation force is about 400 g-f.

4. The wearable medical device of claim 1, wherein customizing the minimum force value comprises obtaining calibration data through a calibration exercise with the patient.

5. The wearable medical device of claim 4, wherein the processing circuitry is configured to periodically initiate the calibration exercise.

6. The wearable medical device of claim 1, wherein customizing the minimum force value comprises conducting a calibration sequence comprising:
detecting application of at least a lower predetermined force threshold of the at least two possible values for the threshold level at a first response button of the at least one response button;
after the detecting, monitoring signals from the first response button over a calibration period of time to determine an activation profile of the patient; and
storing an identification of the minimum force value in the memory.

7. The wearable medical device of claim 6, wherein conducting the calibration sequence further comprises storing the activation profile in the memory.

8. The wearable medical device of claim 6, wherein the calibration sequence is conducted during routine patient interaction with the controller.

9. The wearable medical device of claim 6, wherein conducting the calibration sequence comprises determining a typical force applied to the first response button by the patient.

10. The wearable medical device of claim 1, wherein customizing the minimum force value comprises receiving selection of the minimum force value from two or more predetermined selectable threshold levels.

11. The wearable medical device of claim 1, wherein analyzing the first signal comprises analyzing a first time-series of signals from the force-sensitive sensor of the at least one response button to identify the force value as a force applied over a threshold period of time.

12. The wearable medical device of claim 1, wherein the processing circuitry is further configured to:
prior to monitoring for the input, provide the patient with a notification regarding activation of electrical therapy by the therapy delivery circuit;
wherein monitoring for the input comprises, after registering the input,
verifying the input is to activate a failsafe override of the electrical therapy, and
upon the verifying, delaying the electrical therapy.

13. The wearable medical device of claim 12, wherein verifying the input is to activate the failsafe override of the electrical therapy comprises:
analyzing, over a second predetermined period of time, a plurality of signals from the at least one response button;
identifying, from the plurality of signals, at least one of
a) a pulsed force persisting throughout the second predetermined period of time, each pulse of the pulsed force in the range from the minimum force value to the actuation force, or b) a predetermined pattern of applied forces, each force of the predetermined pattern of applied forces in the range from the minimum force value to the actuation force; and upon the identifying, delaying the electrical therapy.

14. The wearable medical device of claim 1, wherein the actuation force is a force required for actuation of a force-activated switch of the at least one response button.

15. The wearable medical device of claim 1, wherein the one or more cardiac sensing electrodes comprise a plurality of ECG electrodes configured to collect ECG information.

16. The wearable medical device of claim 1, further comprising one or more sensors configured to monitor heart vibrations.

17. The wearable medical device of claim 1, wherein the controller comprises a housing, the at least one response button being mounted to the housing of the controller.

18. The wearable medical device of claim 17, wherein a first response button of the one or more response buttons is disposed on a first surface of a housing of the controller, and a second response button of the one or more response buttons is disposed on a second surface of the housing.

19. The wearable medical device of claim 1, wherein the one or more response buttons comprises a pair of response buttons configured to be concurrently activated.

20. The wearable medical device of claim 19, wherein the pair of response buttons are configured to be concurrently activated via a pinching motion of two fingers of the patient.

* * * * *